United States Patent
Santhanam et al.

(10) Patent No.: US 10,828,243 B2
(45) Date of Patent: *Nov. 10, 2020

(54) METHODS FOR TREATING SKIN

(71) Applicant: AVON PRODUCTS, INC., Suffern, NY (US)

(72) Inventors: Uma Santhanam, Tenafly, NJ (US); Jolanta Idkowiak-Baldys, Montebello, NY (US); Daniel Thorn Leeson, Chatham, NJ (US); Anthony D. Gonzalez, Oak Ridge, NJ (US); Glen T. Anderson, Pleasantville, NY (US)

(73) Assignee: Avon Products, Inc., Suffern, NY (US)

( * ) Notice: Subject to any disclaimer, the term of this patent is extended or adjusted under 35 U.S.C. 154(b) by 193 days.

This patent is subject to a terminal disclaimer.

(21) Appl. No.: 16/106,457

(22) Filed: Aug. 21, 2018

(65) Prior Publication Data

US 2018/0353407 A1 Dec. 13, 2018

Related U.S. Application Data

(63) Continuation of application No. 15/974,106, filed on May 8, 2018, now Pat. No. 10,076,479, which is a continuation of application No. 15/416,791, filed on Jan. 26, 2017, now Pat. No. 9,968,538, which is a continuation of application No. 15/061,678, filed on Mar. 4, 2016, now Pat. No. 9,956,151.

(60) Provisional application No. 62/128,647, filed on Mar. 5, 2015.

(51) Int. Cl.
| | | |
|---|---|---|
| A61K 36/00 | (2006.01) | |
| A61K 8/365 | (2006.01) | |
| A61K 8/67 | (2006.01) | |
| A61K 8/9789 | (2017.01) | |
| A61Q 19/08 | (2006.01) | |

(52) U.S. Cl.
CPC .............. *A61K 8/365* (2013.01); *A61K 8/673* (2013.01); *A61K 8/675* (2013.01); *A61K 8/9789* (2017.08); *A61Q 19/08* (2013.01)

(58) Field of Classification Search
CPC .................................................... A61K 36/00
See application file for complete search history.

(56) References Cited

U.S. PATENT DOCUMENTS

| | | | |
|---|---|---|---|
| 4,826,828 A | 5/1989 | Wilmott et al. | |
| 5,153,230 A | 10/1992 | Manzoor | |
| 5,770,222 A | 6/1998 | Unger et al. | |
| 6,565,864 B2 | 5/2003 | Pillai et al. | |
| 7,469,804 B2 | 12/2008 | Thiebaut | |
| 7,960,437 B2 | 6/2011 | Anderson et al. | |
| 8,398,964 B2 | 3/2013 | Kamei et al. | |
| 8,455,012 B2 | 6/2013 | Florence et al. | |
| 8,517,225 B2 | 8/2013 | Corbellini | |
| 8,523,469 B2 | 9/2013 | Abergel | |
| 8,814,002 B2 | 8/2014 | Pires et al. | |
| 2003/0134781 A1 | 7/2003 | Carmichael et al. | |
| 2003/0198657 A1 | 10/2003 | Menon et al. | |
| 2005/0048140 A1 | 3/2005 | Hines et al. | |
| 2005/0129723 A1 | 6/2005 | Anderson et al. | |
| 2006/0045896 A1 | 3/2006 | Morariu | |
| 2009/0022281 A1 | 1/2009 | Aboujaoude et al. | |
| 2009/0052971 A1 | 2/2009 | Pires et al. | |
| 2009/0176876 A1 | 7/2009 | Ramirez et al. | |
| 2010/0040706 A1 | 2/2010 | Dumas et al. | |
| 2011/0044920 A1 | 2/2011 | Hines et al. | |
| 2011/0087557 A1 | 4/2011 | Yau | |
| 2012/0003332 A1* | 1/2012 | Zheng ................... A61Q 19/00 424/725 |
| 2012/0009233 A1 | 1/2012 | Nixon | |
| 2012/0064136 A1 | 3/2012 | Baker et al. | |
| 2013/0052288 A1 | 2/2013 | Leeson et al. | |
| 2014/0112877 A1 | 4/2014 | Yoko et al. | |
| 2014/0212369 A1 | 7/2014 | Grayson | |

FOREIGN PATENT DOCUMENTS

| | | |
|---|---|---|
| EP | 0631772 A2 | 1/1995 |
| EP | 2820969 A1 | 1/2015 |
| FR | 2924932 A1 | 6/2009 |
| JP | H08176006 A | 7/1996 |
| JP | 2005-1792286 A | 7/2005 |
| WO | 96/37420 A1 | 11/1996 |
| WO | 98/48775 | 11/1998 |
| WO | 01/66080 A1 | 9/2001 |
| WO | 200164166 A1 | 9/2001 |
| WO | 2001066080 | 9/2001 |
| WO | 02/22099 A1 | 3/2002 |
| WO | 02/053125 A2 | 7/2002 |
| WO | 2008/106177 A2 | 9/2008 |
| WO | 2012/005876 A2 | 1/2012 |
| WO | 2014049561 A2 | 4/2014 |
| WO | 2014163896 A1 | 10/2014 |

OTHER PUBLICATIONS http://7daysofwonder.com, downloaded from Internet Feb. 25, 2016 (2016).
http://variblend.com, 40mm VariBlend MidiMix Variable Dispenser, 2 pages (2014).
VivaWoman, "Do we Need to Rotate Skin Care Products," 3 pages (2009).

* cited by examiner

*Primary Examiner* — Qiuwen Mi
(74) *Attorney, Agent, or Firm* — Brian P. McCloskey

(57) ABSTRACT

Provided are methods of treating skin with at least two alternating treatment modalities to improve the health and/or diminish signs of aging. Some methods according to the present invention may comprise topically applying at least two separate compositions, in a sequential, rotating, or alternating fashion to overcome adaptation, tolerance, or sensitization phenomena.

10 Claims, 15 Drawing Sheets

| MONTH | | | | | | |
|---|---|---|---|---|---|---|
| SUN | MON | TUES | WED | THUR | FRI | SAT |
| | 1 | 2 | 3 | 4 | 5 | 6 |
| | A | A | A | A | A | A |
| 7 | 8 | 9 | 10 | 11 | 12 | 13 |
| A | B | B | B | B | B | B |
| 14 | 15 | 16 | 17 | 18 | 19 | 20 |
| B | A | A | A | A | A | A |
| 21 | 22 | 23 | 24 | 25 | 26 | 27 |
| A | B | B | B | B | B | B |
| 28 | 29 | 30 | 31 | | | |
| B | A | A | A | | | |

FIGURE 3

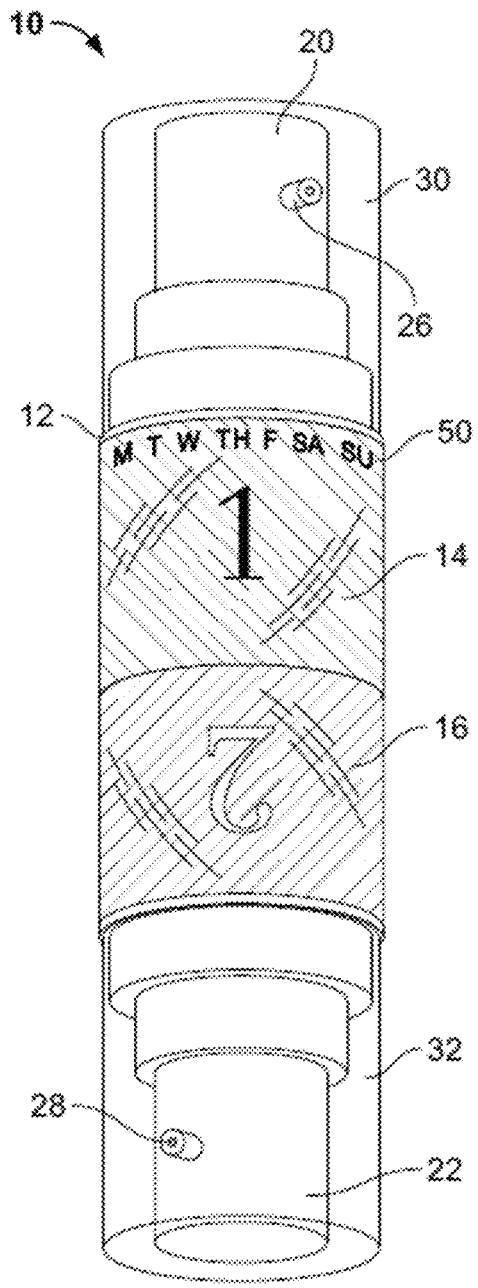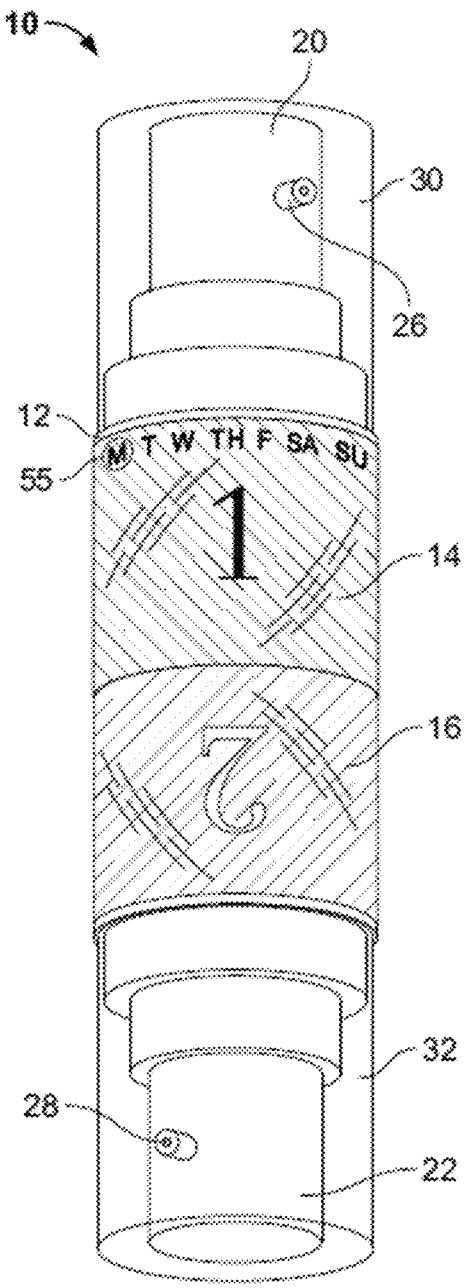
FIGURE 12A                    FIGURE 12B

METHODS FOR TREATING SKIN

CROSS-REFERENCE TO RELATED APPLICATIONS

This application is a continuation of, and claims priority under 35 U.S.C. § 120 to U.S. patent application Ser. No. 15/974,106 filed May 8, 2018 and U.S. patent application Ser. No. 15/416,791 filed Jan. 26, 2017 and patent application Ser. No. 15/061,678 filed Mar. 4, 2016, which claims priority under 35 U.S.C. § 119(e) to U.S. Provisional Patent Application Ser. No. 62/128,647, filed Mar. 5, 2015, the entire contents each of the foregoing applications are hereby incorporated by reference herein.

FIELD OF INVENTION

The invention relates generally to methods for reducing signs of aging and/or improving the health of human skin. More particularly, the invention relates to rotational, serial or alternating use of two or more different treatments to improve the appearance of skin, including remediating the signs of aging. The two or more two different treatment modalities may comprise, without limitation, topical application of compositions containing skincare actives, use of devices, for example, to impart mechanical or electromagnetic energy to the skin, application of masks (which may be active-eluting), subcutaneous injection, oral administration of actives, and chemical peels. The treatment modalities may be carried out at least once a day for a treatment period that may range from 1-31 days, and then the treatment modalities are alternated or rotated serially.

BACKGROUND

Numerous skincare products have been developed for improving the appearance of human skin. Many of the more effective methods employ topically applied compositions containing one or more active ingredients known to beneficially affect the skin. For example, compositions containing retinoids, particularly retinol, have proven to be effective in combating fine lines, wrinkles and other indications of skin aging such as sagging. Topically applied retinoids promote the formation of collagen and elastin in the skin. Compositions having retinoids may be used to treat a myriad of unwanted skin conditions, such as acne and wrinkles. However, the benefits of retinol therapy are known to plateau with prolonged use in some individuals.

Phytol is another active agent that is known to promote skin health and remediate or diminish signs of skin aging. A composition for enhancing the appearance of skin comprising both phytol and retinol is described in U.S. Pub. 2003/0198657 to Menon, the disclosure of which is hereby incorporated by reference herein.

It has been recognized that skin may become accustomed to cosmetic products, and the observable benefits to skin may begin to decline after an initial period of treatment. It has also been observed by dermatologists in clinical trials that skin can build up a tolerance to retinoids, and using higher concentrations of retinoid-containing compositions over time might be needed to maintain the desired effectiveness in some individuals. This phenomenon is analogous to adaptation, which is well-described in biological systems. For example, on a cellular level, stimulation of receptors leads to desensitization and a decreased response. A period of resensitization or "rest" is needed before the same level of response can be seen again.

It is therefore an object of the present invention to provide methods of treating skin that overcome the tolerance problem and/or provide enhanced efficacy and/or improve the health and/or appearance of human skin. It is a further object of the present invention to provide treatments for human skin involving the rotational, serial and/or alternating use of at least two distinct treatment modalities. It is a further object of the present invention to provide methods for improving the health and/or appearance of human skin involving the rotational, serial and/or alternating topical application of at least two skincare compositions.

The foregoing discussion is presented solely to provide a better understanding of nature of the problems confronting the art and should not be construed in any way as an admission as to prior art nor should the citation of any reference herein be construed as an admission that such reference constitutes "prior art" to the instant application.

SUMMARY OF INVENTION

In accordance with the foregoing objectives and others, the present invention provides methods for improving one or more signs of dermatological aging of human skin and/or improving the health of human skin, the methods comprising alternating/rotating between a plurality (e.g., two, three, four, five, six, seven, or more) different treatment modalities. Each treatment modality is administered for a period of time (e.g., at least once daily for 1-31 days), which may be the same or different from the period of time of treatment for each of the other treatment modalities. The treatment modalities may include application of topical compositions to the skin, application of mechanical or electromagnetic energy (e.g., ultrasound, vibration, light (visible, infrared, etc.)) to the skin, mechanical or chemical desquamation (e.g., microdermabrasion, chemical peel, etc.), application of masks to the skin (which may optionally elute skincare actives to the skin), oral administration of actives, etc. The treatment modality may include allowing the skin to "rest," by not treating it in any particular manner, other than customary routine washing and/or moisturizing. In some implementations, at least one of the plurality of treatment modalities entails topical application of a skincare active ingredient to an area of skin (e.g., the face) at least once daily for a period of 1-31 days. In some implementations, at least two of the plurality treatment modalities entail topical application of a skincare active ingredient to an area of skin (e.g., the face) at least once daily for a period of 1-31 days, wherein the skincare actives and treatment periods may be different from one another. In some implementations, at least one of the plurality of treatment modalities entails application of mechanical or electromagnetic energy to an area of skin (e.g., the face) at least once daily for a period of 1-31 days. In some implementations, at least one of the plurality treatment modalities entails exfoliation (e.g., chemical or mechanical) of an area of skin (e.g., the face) at least once daily for a period of 1-31 days, for example, using a chemical peel (e.g., phenol), microdermabrasion, or with a topical composition comprising an effective amount of a desquamating agent. In some implementations, the method comprises the use of at least two treatment modalities, wherein a first composition is applied topically to an area of skin (e.g., the face) one or more times daily for a first period of time (e.g., 1-31 days), followed by topical application to the same area of skin of a second composition one or more times daily for a second period of time (e.g., 1-31 days).

Without wishing to be bound by any particular theory, it is believed that the rotational treatment regimen overcomes, at least in part, adaptation and/or toleration phenomena whereby the effect of certain actives or treatments diminishes or plateaus over time. It is also theorized that the rotational treatments may act cooperatively and/or synergistically whereby one treatment modality enhances the efficacy of the other. For example, a desquamation treatment is contemplated to improve penetration of a subsequently applied active, or an anti-inflammatory treatment is contemplated to reduce erythema associated with retinol use and consequently permit higher levels or more frequent application of retinoids.

In one aspect of the invention, methods of treating skin to improve the health and/or appearance thereof are provided comprising administering a first treatment modality (e.g., topically applying a first composition comprising an active agent) to an area of skin in need thereof at least once daily for a first period of time (e.g., a predetermined period of time), typically from 1-31 days, or from 2-31 days, or from 3-31 days, or from 4-31 days, or from 5-31 days, or from 6-31 days, or from 7-31 days, or from 1-7 days, or from 2-7 days, or from 3-7 days, or from 4-7 days, or from 5-7 days, or 7 days, etc. The period of time may be "predetermined," by which is meant that prior to beginning the regimen the user determines or is instructed (e.g., by written instruction accompanying the product or obtained electronically on a computer) to use the treatment modality (e.g., topically apply a skincare composition) daily for a fixed number of consecutive days. Alternatively, the period of time may be determined by the user's response and/or reaction to daily use of the first treatment modality (e.g., topical application of the first composition). For example, the first period of time may begin on the first day of administration/application and end on the appearance of irritation and/or redness, or may end on when there are observable improvements and/or reductions in a sign of skin aging, or may end on the onset of an efficacy plateau, etc. In some implementations, the first treatment modality (e.g., topical application of a skincare composition) is used on the same area of skin for at least two, three, four, five, six, seven or more consecutive days. In other implementations, the first treatment modality (e.g., topical application of a skincare composition) is used for only one day. In other implementations, the first treatment modality (e.g., topical application of a skincare composition) is used daily for seven days.

The first period of time may be followed by a second period of time in which the first treatment modality is discontinued and/or use of a second treatment modality is initiated. For example the first treatment modality may comprise topical application of a first composition (comprising a first active agent) for a first period of time, and thereafter: (i) the first composition is not topically applied to the same area of skin daily for a second period of time, (ii) the first composition continues to be applied to the same area of skin daily but in altered amounts (e.g., the dose ($mg/cm^2$) is increased or decreased relative to the first period of time) or altered frequency (e.g., applied more times or less times per day relative to the first period of time) for a second period of time, and/or (iii) a second composition is topically applied (e.g., at least once daily) to the same area of skin for a second period of time. In one embodiment, the first treatment modality is discontinued during the second period of time.

The second period of time is typically from 1-31 days, or from 2-31 days, or from 3-31 days, or from 4-31 days, or from 5-31 days, or from 6-31 days, or from 7-31 days, or from 10-31 days, or from 14-31 days, or from 5-31 days, or from 6-31 days, or from 7-31 days, or from 1-7 days, or from 2-7 days, or from 3-7 days, or from 4-7 days, or from 5-7 days, or from 7 days, etc. In some implementations, a second treatment modality (e.g., topical application of a skincare composition) is administered to the same area of skin for at least one, two, three, four, five, six, seven or more consecutive days. In some embodiments the second period of time is shorter than, equal to, or longer than the first period of time. In some embodiments, the second period of time is one day. In some embodiments the second period of time is seven days. The second period of time may be predetermined (e.g., according to written instructions) or may be determined by the user's response and/or reaction to daily use/application of the second treatment modality. The second period of time typically begins on the day following the last day of the first period of time, although it is contemplated that the end of the first period of time and the beginning of the second period of time may be separated by one, two, three, four, five, six, or seven days or more, which may be a predetermined period of time, for the skin to "rest" without treatment with the first or second treatment modalities. This could entail treating the skin only with a composition having no skin actives (e.g., with only moisturizer treatment) or applying nothing at all during that time. It is also contemplated that the second period of time may partially (but not completely) overlap with the first period of time such that the first and second modalities are administered to the same area of skin daily for a number of days (e.g., one day, two days, three, days, etc.). The second period of time may therefore overlap with, be subsumed by, or be consecutive with the first period of time, or may follow the first period of time after an interval of a day or more. The second treatment modality may comprise topical application of a second skincare composition that is different from the first skincare composition. For example, if the first skincare composition comprises an effective amount of a retinoid (e.g., retinol), then the second skincare composition may, in some embodiments, comprise a different retinoid, a different amount of the same retinoid, or may be free of retinoids (e.g., retinol). In some implementations, the second treatment regimen may entail the absence of treatment, by which is meant that no composition is topically applied to the skin. To illustrate, one treatment regimen according to the invention may comprise alternating between a first modality comprising topical application of a retinol formulation, followed by a second modality comprising topical application of a second formulation that does not comprise retinol (or any retinoid), and thereafter repeating those steps one or more additional times.

After completion of the second treatment modality, the regimen may continue with re-administration of the first treatment modality to the same area of skin for said first period of time. The first period of time may commence on the day following the last day of the second period of time. Alternatively, the second period of time may be followed by a "rest" period (as described above) prior to commencing the first treatment modality. In another embodiment, the second treatment modality may be followed (on the next day or after any period of "rest") by a third treatment modality for a third period of time.

The regimen may continue in this fashion using any number of treatment modalities. For example, in one embodiment of the invention, seven different treatment modalities are administered to the individual for seven periods of time in sequence. The periods of time according to this embodiment may range from 1-31 days, more typically, from 1-7 days, or from 1-3 days, or 1 day. In one embodiment, the treatment regimen comprises seven different treatment modalities, each of which are administered for at least one day (or for only one day) during a period of seven consecutive days, with the proviso that no two days have the identical treatment regimen.

In various embodiments in which two treatment modalities are employed, the modalities may be indicated as "A" and "B," respectively, where "A", "B" may each represent a topical composition, identify a treatment material or materials and/or modality of treatment administration, duration, intensity, etc., repeated at different intervals (per application; per day; per week; etc.). In some embodiments, the treatment regimen may be represented as $(AB)_n$, where modalities A and B are employed sequentially, and then the process is repeated n–1 times (where n is typically greater than 2, or greater than 3, or greater than 4, or greater than 8, or greater than 12, etc.). For example, in the case where n=4, this may be represented as ABABABAB. Additional treatment modalities may also be included. For example, in the case where a third treatment modality "C" is included, the regimen may represented as $(ABC)_n$, where modalities A, B, and C are employed sequentially, and then the process is repeated n–1 times. For example, in the case where n=4, this may be represented as ABCABCABCABC. Additional treatment modalities may also be included. In another embodiment, the treatment modalities may be interspersed with rest periods in which no actives or non-active skin care formulations are utilized.

In some embodiments, at least one of the pluralities of treatment modalities comprises topical application of a composition comprising an effective amount of at least one skincare active. The active is usually dissolved or dispersed in a physiologically compatible carrier (e.g., an emulsion, oil, gel, serum, etc.). The effective amount of the active may, for example, comprise from about 0.0001% to about 25% (w/w) based on the weight of the entire composition, more typically, from about 0.001% to about 5% by weight (or from about 0.01-1% or 0.1-0.5% by weight). The composition may include additional adjuvants and excipients, such as film formers, oils, resins, elastomers, waxes, thickeners and rheology modifiers, gellants, stabilizers, emollients, conditioning agents, humectants, chelating agents, pH adjusters, preservatives, fragrances, fillers and powders, colorants and optical modifiers, sunscreens, etc. The vehicle may comprise water or it may be anhydrous or substantially anhydrous. The vehicle may comprise one or more oils, including ester oils, vegetable oils, fatty alcohols, hydrocarbon oils, mineral oils, polyolefin oils, silicone oils, and the like.

In one embodiment, at least one of the plurality of treatment modalities comprises topical application of a composition comprising an effective amount (e.g., from about 0.05% to about 5% (w/w)) retinoid (e.g., retinol, retinaldehyde, retinyl palmitate, etc.) at least once daily (or once daily, etc.) for a first period of time from 1 day to 31 days, more typically, from 2-31 days, or from 3-14 days, or from 5-10 days, or for 7 days. In one implementation, the first composition comprises an effective amount of a retinoid (e.g., retinol). In another implementation, the second composition comprises an effective amount of a retinoid (e.g., retinol). In one implementation, the first composition comprises an effective amount of a retinoid (e.g., retinol) and the second composition does not comprise an effective amount (e.g., from about 0.05% to about 5% (w/w)) of retinoid (e.g., retinol). In another implementation, the second composition comprises an effective amount of a retinoid (e.g., retinol) and the first composition does not comprise an effective amount (e.g., from about 0.05% to about 5% (w/w)) of retinoid (e.g., retinol).

In some implementations, at least one of the plurality of treatment modalities entails topical application of an effective amount of a retinoid (e.g., retinol), at least once daily (or once daily) for a first period of time from 1 day to 31 days, or from 2-31 days, or from 3-14 days, or from 5-10 days, or from 1-7 days or from 1-5 days, or from 1-3 days, or for one day. In one implementations, at least one of the plurality of treatment modalities entails topical application of an effective amount of a retinoid (e.g., retinol), at least once daily (or once daily, for example, at night) for seven consecutive days.

In one implementation, the first treatment modality (e.g., topical application of a first composition comprising a skincare active) is administered daily for five consecutive days (e.g., Monday-Friday) and the second treatment modality (e.g., topical application of a second composition comprising a different skincare active), which is different from the first treatment modality, is administered daily for the following two days (e.g., Saturday-Sunday). In another implementation, the first treatment modality (e.g., topical application of a first composition comprising a skincare active) is administered daily for seven consecutive days (e.g., Monday-Sunday) and the second treatment modality (e.g., topical application of a second composition comprising a different skincare active), which is different from the first treatment modality, is administered daily for the following seven consecutive days (e.g., Monday-Sunday). The regimen may be repeated a plurality of times, including at least one, two, three, four or more additional times, and typically until an improvement in the health and/or appearance of skin is noted. The first treatment modality may involve topical application of a composition comprising an effective amount (e.g., 0.05% to 5% by weight) of a retinoid, such as retinol or retinyl palmitate. The second treatment modality may involve topical application of a second composition comprising, for example, an effective amount of a skin care active other than a retinoid. In one implementation, the second composition comprises an effective amount of alpha hydroxy acid. In one implementation, the second composition comprises an effective amount of an antioxidant. In one implementation, the second composition comprises an effective amount of a botanical extract (e.g., *Tiliacora triandra* extract, including hydroponically grown variants). In another implementation, the second composition comprises moisturizers, emollients, and/or humectants and may comprise additional actives or may be free of additional actives (e.g., phytol, glycolic acid, and/or niacinamide). In another implementation, the second composition does not comprise an effective amount of retinoids (e.g., retinol) or is free of retinoids (e.g., retinol).

In some embodiments, the first topical cosmetic composition may comprise at least one skin active that has the effect of improving the appearance and/or health of skin, including, without limitation, diminishing the appearance of signs of skin aging (e.g., chronological, hormonal, environmental, and/or photo-aging). In some embodiments, the first active agent may be a substance (e.g., small molecule, amino acid, protein, peptide, nucleic acid, extract, etc.) that increases collagen, pro-collagen, elastin, glucosaminoglycan (GAG) and/or hyaluronic acid production in the skin and/or reduces pigmentation in the skin and/or modulates (increases or decreases) lipolysis or lipogenesis in adipocytes. The active agent may be, without limitation, an agent that improves tautness of skin (e.g., reduces sagging), diminishes the appearance of wrinkles and/or fine lines (e.g., crow's feet, feathering, etc.), thickens thinning skin, improves (e.g., evens out) skin tone, reduces the appearance of localized areas of pigmentation (e.g., sun spots, freckles, liver spots, age spots, etc.), reduces the appearance of dark circles under the eyes, and/or reduces the appearance of cellulite, etc. In some embodiments, the first composition may comprise one or more of the following: collagenase inhibitors, elastase inhibitors, collagen upregulators/stimulators, pro-collagen upregulators/stimulators, elastase upregulators/stimulators, hyaluronic acid upregulators/stimulators, tyrosinase inhibitors, melanosome transferase inhibitors, melanogenesis inhibitors.

In some embodiments, the active agents may comprise one or more of the following: retinoids (e.g., retinol and $C_{2-20}$ esters thereof, such as retinol palmitate, retinol acetate and retinol propionate, retinaldehyde, 9-cis retinoic acid, 13-cis retinoic acid, all-trans retinoic acid, phytanic acid, Vitamin A, and esters and salts of any of these, etc.), α-hydroxy acids (e.g., glycolic acid, lactic acid, citric acid, etc.), β-hydroxy acids (e.g., salicylic acid), salicylates, 5-α-reductase inhibitors (linolenic acid, linoleic acid, finasteride, etc.), vitamins (e.g., vitamins A, B, C, E, etc., and $C_{2-20}$ esters thereof), PPAR-γ inhibitors, anti-inflammatories (e.g., TNF-α inhibitors), antioxidants (e.g., ascorbic acid, astaxanthin, beta-carotene, catechins, curcumin, ellagic acid and gallic acid derivatives (e.g., propyl gallate), ferulic acid derivatives (e.g. ethyl ferulate, sodium ferulate), glutathione (GSH), green tea extract, hexylresorcinol, idebenone, α-lipoic acid, lycopene, phytol, phytanic acid, TDPA and esters (e.g., dilauryl) thereof, thioglycolic acid, reductic acid; rosmarinic acid; tannic acid; tetrahydrocurcumin; tocopherol and its derivatives, ubiquinone, uric acid and $C_{2-20}$ esters of any of the thereof), phytochemicals (e.g., flavonoids and carotenoids), phytoalexins, stilbenoids (e.g., resveratrol), botanicals, Advanced Glycation End Product (AGE) inhibitors/reversers (e.g., TDPA), purines; estrogen synthetase stimulating compounds (e.g., xanthine and caffeine and derivatives), aminoacids (e.g., L-arginine, L-aspartic acid, L-glutamine, L-glycine, L-lysine, L-histidine, L-alanine, L-threonine, L-glutamic acid, L-taurine, L-proline, L-serine, etc., or $C_{2-20}$ esters or amides and derivatives thereof, including enantiomers) and derivatives thereof (e.g., carnitine, N-acetyl Tyrosinamide, etc.), di-peptides (e.g., carnosine), and oligopeptides and $C_{2-20}$ (e.g., palmitoyl) esters or amides thereof (e.g., palmitoyl oligopeptides), desquamating agents (e.g., glycolic acid, salicylic acid, imidopercarboxylic acids, jasmonic acid, gentisic acid, 3,6,9-trioxaundecanedioic acid, etc., and derivatives of any of these), keratolytics (e.g., allantoin, lactic acid, urea, etc.), astringents (e.g., Witch hazel), antipruritic agents (e.g., camphor, menthol, etc.), anti-acne agents (e.g., salicylic acid, sulfur, benzoyl peroxide, triclosan, etc.), steroids, including corticosteroids (e.g., hydrocortisone) and sterols (e.g., β-sitosterols, phytosterols, such as *Glycine soja* sterols, pomegranate sterols, *Brassica campestris* sterols, canola sterols, etc.), soy isoflavone glycosides (e.g., genistin, daidzin, and glycitin) and aglycones (e.g., genistein, daidzein, and glycitein), depigmenting agents (e.g., hydroquinone, licorice extract, kojic acid, niacinamide, etc.), pigmenting agents (e.g., dihydroxyacetone), barrier function enhancing agents (e.g., ceramides, such as ceramide-2, glycerides, cholesterol and its esters, alpha- and omega-hydroxy fatty acids and esters thereof, etc.), serine protease inhibitors (e.g., soy proteins), and combinations thereof.

In various, non-limiting embodiments, the active agent may be a substance that modulates (e.g., upregulates, down regulates, stimulates, inhibits, etc.) expression or activity of one or more of the following: retinoic acid receptor (RAR), retinoid X receptor (RXR), Carnitine palmitoyltransferase I (CPT-1), PLOD-2, Thymosin-β4, tenascin-X, WIPI-1, Nesprin-2, MAGP-1, tyrosinase, desmogleins 1 and 3, fibroblast growth factors (FGFs), paxillin, collagen 1, C-Reactive Protein (CRP), Calcitonin gene related peptide (CGRP), sirtuins (SIRT1 protein), filbrillin-1, PPAR (e.g., α, γ, etc.) receptors, stearoyl CoA desaturase (SCD1), adiponectin, cyclooxygenase-2 (COX-2) enzyme, metallothioneins, Lysyl oxidase like-1 (LOXL1), β-1-integrin, cytokines (e.g., I-CAM, IFN-γ, IL1-β, IL12, IL6, IL8, IL2, IP10, TNF-α, TNFr2, etc.) histamine (e.g., $H_1$, $H_2$, etc.), adipose septa (e.g., receptorasporin, biglycan, decorin, dermatopontin, fibromodulin, fibronectin, galectin-1, laminin beta 2, lumican, MAGP-4, mimecan (osteoglycin), nidogen-1, nidogen-2, or prolargin), DICKKOPF-1, paxillin, fibroblast growth factor receptor 1 (FGFR1), alpha-2-adrenergic receptor, beta-adrenergic receptor, phosphodiesterase, adenylate cyclase activator, serine proteinase (e.g., trypsin inhibitor, neutrophil elastase, etc.), matrix metalloproteinase (e.g., gelatinase B), fructosamine-3-kinase (FN3K or FN3K RP), matriptase MT/SP1, Monoamine Oxidase B (MAOB), growth factors (e.g., bFGF, PDGF, VEGF, etc.), Human tissue Kallikreins (KLKs, e.g., KLK-5), Calcineurin, etc.

In some embodiments, either the first or second composition comprises a $C_{20}$-$C_{25}$ terpene alcohol (e.g., phytol) or a metabolite therefore (e.g., phytanic acid). In some embodiments, either the first or second composition comprises a retinoid (e.g., retinol or retinol palmitate). In some embodiments, either the first or second composition comprises a $C_{20}$-$C_{25}$ terpene alcohol (e.g., phytol) or a metabolite therefore (e.g., phytanic acid) and the other composition comprises a retinoid (e.g., retinol).

In some implementations, either the first or second composition comprises a $C_{20}$-$C_{25}$ terpene alcohol (e.g., phytol) or a metabolite therefore (e.g., phytanic acid), and the other composition comprises a retinoid (e.g., retinol). The first and second compositions are applied in a serial, sequential, rotating, and/or alternating fashion. Typically, the alternating treatments are carried out without a gap in between them, such that one begins on the day following the end of the other. Typically, the first period of time will be from about one day to about one month (or from 3-20 days or from 5-10 days) and the second period of time will be from about one day to about one month (or from 3-20 days or from 5-10 days). The compositions may be applied in either order (e.g., phytol treatment period followed by retinol treatment period, or retinol treatment period followed by phytol treatment period), and the method may be repeated any additional number of times (e.g., once, twice, thrice, etc.), to achieve any number of alternating treatments with said first and second compositions, and ideally for long enough to achieve a visible improvement in the health and/or appearance of skin (e.g., a reduction in the number and/or depth of wrinkle or fine lines). In some implementations, the treatment is continued for at least 4 weeks, at least 8 weeks, at least 12 weeks, or more.

In one aspect, a method for diminishing the appearance of dermatological signs of aging (e.g., fine lines and/or wrinkles and/or thinning skin and/or reducing unwanted pigmentation and hyperipgmentation and/or sagging skin, etc.) and/or improving the health of human skin (e.g., improving barrier function, etc.) is provided, the method comprising the steps of: (1) topically applying to an area of skin in need of such treatment an effective amount (e.g., from about 0.001-5% by weight) of a $C_{20}$-$C_{25}$ terpene alcohol (e.g., phytol) or metabolite therefore (e.g., phytanic acid) containing composition for a first period of time (e.g., 1-31 days, or 3-20 days, or 5-10 days, or 7 days, etc.); and thereafter (2) topically applying to the same area of skin an effective amount (e.g., from about 0.001-5% by weight) of a retinoid (e.g., retinol) containing composition for a second period of time (e.g., 1-31 days, or 3-20 days, or 5-10 days, or 7 days, etc.). The steps may be performed in either order. Typically, the two periods of time end and begin on consecutive days, such that there is not an intervening day without treatment. In some implementations, however, there may be a predetermined number of intervening days (e.g., one, two, three, etc.) between the two periods of treatment. The method may further comprise repeating steps (1) and (2) for one, two, three, four or more additional times, ideally until an improvement in skin health and/or a reduction in the dermatological signs of aging is noted. The method may be carried out chronically or indefinitely for continued treatment and/or prophylaxis. In some implementations, the method is for reducing the appearance of wrinkles and/or fine lines, including reducing the number of such wrinkles and/or fine lines, reducing the depth of such wrinkles and/or fine lines, or forestalling the development or, or progression of such wrinkles and/or fine lines. In some implementations, the method is for reducing unwanted pigmentation in the skin, including without limitation, reducing age spots, freckles, sun spots, and the like, or for reducing the mottled appearance of skin and/or evening skin tone.

In another aspect, a method for diminishing the appearance of dermatological signs of aging (e.g., treating wrinkles and/or fine line, and/or treating skin sagging/improving elasticity and/or evening skin tone and/or reducing unwanted pigmentation) is provided, comprising the steps of: (1) topically applying to an area of skin in need therefore an effective amount (e.g., from about 0.001-5% by weight) of a phytol-containing composition for a first period of time (e.g., e.g., 1-31 days, or 3-20 days, or 5-10 days, or 7 days, etc.); and topically applying to the same area of skin an effective amount (e.g., from about 0.001-5% by weight) of a retinol-containing composition for a second period of time (e.g., e.g., 1-31 days, or 3-20 days, or 5-10 days, or 7 days, etc.), and (3) repeating steps (1) and (2) for at least one (e.g., two, three, four or more) additional times (or repeating until an improvement is noted). Steps (1) and (2) may be performed initially in either order and repeated in that same order in step (3). The two periods of time may end and begin on consecutive days, such that there is not an intervening day without treatment, or there may be a predetermined number of intervening days (e.g., one, two, three, etc.) between the two periods of treatment. The method may be carried out for at least one, two, four, eight, or twelve weeks or longer, until a benefit is seen, including chronic or indefinitely continued treatment for maintenance and/or prophylaxis.

In one aspect of the invention, a method for diminishing dermatological signs of aging in human skin is provided comprising, in any order, the steps of (1) topically applying to an area of the skin in need thereof (e.g., skin of the face, neck, chest, hands, etc.), at least once daily (e.g., once daily at night or in the morning), a first skin treatment composition comprising, in a physiologically compatible vehicle (e.g., an oil-in-water emulsion comprising from 0.01-10% by weight of an emulsifier), an effective amount (e.g., 0.01% to about 1% by weight) of a retinoid (e.g., retinol) for a first period of time comprising from 1 to 31 days (e.g., from 2-15 days, or for seven days); (2) implementing a second treatment modality for a second period of time comprising from 1 to 31 days (e.g., from 2-15 days, or for seven days); and (3) repeating steps (1) and (2) for a number of times (e.g., four or more) sufficient to diminish said dermatological signs of skin aging (e.g., treat wrinkles and/or fines lines and/or diminish appearance of unwanted pigmentation). In one implementation, the second treatment modality comprises topically applying to said same area of skin, at least once daily (e.g., once daily at night or in the morning), a second skin treatment composition that is different from said first skin treatment composition (e.g., it does not comprise an effective amount of a retinoid such as retinol), and which may comprise, in a physiologically compatible vehicle (e.g., an oil-in-water emulsion comprising from 0.01-10% by weight of an emulsifier), one or more skin active agents, including without limitation, α-hydroxy acids (e.g., glycolic acid, lactic acid, citric acid, etc.) and/or antioxidants (e.g., ascorbic acid, beta-carotene, hexylresorcinol, tocopherol and its derivatives, including acetate esters, phytol, phytanic acid, and thiodipropionic acid and its di-alkyl esters, including di-lauryl esters), such as, for example, from about 0.01% to about 10% by weight phytol, from about 0.01% to about 10% by weight glycolic acid, and/or from about 0.01% to about 10% by weight thiodipropionic acid or esters (e.g., di-lauryl esters) thereof. Typically, in the practice of the method according to this embodiment, the first and second periods of time are consecutive such that one begins on the day following the last day of the other, and in one particular implementation, both the first and second periods of time are seven days.

Typically, the method is repeated for a period of time sufficient to improve the health of skin and/or achieve a desired benefit of diminishing the signs of aging in the skin (e.g., reduction in number or severity of wrinkles and/or fine lines, reduced sagging/improved elasticity, thicken thinning skin, and/or more even skin tone, and/or reducing unwanted pigmentation, etc.). This may entail topical application at least once daily for at least one week, at least two weeks, at least four weeks, or at least eight weeks or more. In some embodiments, the compositions are applied directly to a specific site of the skin (i.e., directly onto a wrinkle, directed to a hyperpigmented spot, under the eyes, etc.). In some embodiments, the first and/or second compositions will be applied to the skin in an amount from about 0.001 to about 100 mg/cm$^2$, more typically from about 0.01 to about 20 mg/cm$^2$, or from about 0.1 to about 10 mg/cm$^2$.

In yet another aspect of the invention, a kit is provided comprising: (i) a first composition comprising a topically acceptable vehicle (e.g., emulsion, gel, or serum) and an effective amount (e.g., from about 0.001-5% by weight) of a retinoid (e.g., retinol or its esters, such as acetate, propionate, palmitate, etc., retinaldyhede, retinoic acid, etc.); and (ii) a second composition comprising a topically acceptable vehicle (e.g., emulsion, gel, or serum) and an effective amount (e.g., from about 0.001-5% by weight) of a skin active, such as an antioxidant, alpha-hydroxy acid, botanical, etc., including, for example, phytol and/or TDPA (or its di-alkyl esters) and/or glycolic acid, and (iii) written instructions for topically applying said first and second compositions, in any order, in alternating fashion, such that the first composition is applied at least once daily for a first period of time and said second composition is applied at least once daily for a second period of time. The instructions may further indicate that the alternating treatments are carried out without a gap in between them, such that one begins on the day following the end of the other, or may provide for a predetermined gap (e.g., one day, one week, etc.), between the end of one treatment period and the beginning of the next. The instructions may indicate that the first period of time will be from about one day to about one month (or from 3-20 days or from 5-10 days or 7 days) and the second period of time will be from about one day to about one month (or from 3-20 days or from 5-10 days or 7 days). The instructions may also indicate that the compositions may be applied in either order (e.g., first treatment period followed by second treatment period, or, alternatively, second treatment period followed by first treatment period). The instructions may indicate that the treatments may be repeated. The instructions may specify any number of alternating treatments (e.g., one, two, three, four, or more) with said first and second compositions. The instructions may indicate that the treatment should be carried out for long enough to achieve a visible improvement in the health and/or appearance of skin (e.g., a reduction in the number and/or depth of wrinkle or fine lines, reduction in unwanted pigmentation, etc.). In some implementations, the instructions indicate that the treatment is continued for at least 4 weeks, at least 8 weeks, at least 12 weeks, or more. The written instructions may be included on the container, associated packaging, or on a website. In the case where the instructions are on a website, the container or packaging will comprise written instructions for accessing the website (including, for example, a QR code, etc.). The first and second compositions may be physically separated from one another, for example, in separate containers, or within separate reservoirs within the same container. The first and second compositions each may be provided in amounts corresponding to the same predetermined number of treatments (e.g., equivalent number of doses). The first and second compositions each may be contained in a plurality of containers corresponding to an individual dose. The first and second compositions each may be contained in containers bearing written instructions for the period of use of each composition. The first and/or second compositions may further include a sunscreen.

In yet another aspect of the invention, a skincare product is provided comprising a container comprising a first reservoir containing a first skin treatment composition and a second reservoir containing a second skin treatment composition, different from said first skin treatment composition, a first pump in fluid communication with the first reservoir for dispensing said first skin treatment composition, and a second pump in fluid communication with the second reservoir for dispensing said second skin treatment composition, wherein each pump optionally is covered by a removable cap. The container may be in the shape of an elongate cylinder, having the first pump and second pump disposed on opposite ends thereof. The first and second reservoirs may or may not be separable from one another. The container may comprise (e.g., on a visible surface thereof or on a label affixed thereto) visible identifiers for distinguishing the first and second reservoirs. In one embodiment, the identifiers may comprise alpha-numeric symbols (e.g., a number or letter identifying one reservoir/composition and a different number or letter identifying the other reservoir/composition). In another embodiment, the identifiers may comprise a visual identifier, such as different colors, patterns, artworks, pictures, etc. (e.g., one color identifying one reservoir/composition and a different color identifying the other reservoir/composition). Combinations or alpha-numeric identifiers and other visual identifiers may also be used. In another embodiment, the identifiers comprise a symbol other than an alpha-numeric symbol. The product will typically include, either on the label, packaging, associated website, etc., written instructions for topically applying to an area of skin in need thereof an amount of said first skin treatment composition (e.g., at least once daily) for a first period of time comprising from 1-31 or from 2-15 days or 7 days, followed by topically applying to said area of skin said second skin treatment composition (e.g., at least once daily) for a second period of time comprising from 1-31 or from 2-15 days or 7 days). In some implementations, the first composition may comprise a topically acceptable vehicle (e.g., an oil-in-water emulsion with 0.01-10% by weight of an emulsifier) and an effective amount (e.g., from about 0.001-5% or 0.05-1% by weight) of a retinoid (e.g., retinol or its esters, such as acetate, propionate, palmitate, etc., retinaldyhede, retinoic acid, etc.), typically retinol; and (ii) a second composition comprising a topically acceptable vehicle (e.g., an oil-in-water emulsion with 0.01-10% by weight of an emulsifier) and an effective amount (e.g., from about 0.001-5% or 0.05-1% by weight) of a skin active, such as an antioxidant, alpha-hydroxy acid, botanical, etc., including, for example, phytol and/or TDPA (or its di-alkyl esters) and/or glycolic acid. The first and second skin treatment compositions may, for example, each have a viscosity between about 10,000 cps and 250,000 cps (e.g., between 25,000 cps and 150,000 cps, or between 50,000 and 100,000 cps when measured at a shear rate of 10 $s^{-1}$ at 25° C., and may have a similar or distinct attribute selected from tactile feel, scent, color, or other visual attribute and/or the perception of cooling or heating. In some implementations, the viscosity of said second composition is within ±50% or ±40% or ±30% or ±20% or ±10% or ±5% of the viscosity of said first composition. In some embodiments, the product will include visible identifiers indicating each day of the week, for example, printed on a label affixed to the container. For example, the product may have a label adhered to the container, and the label may have the letters such as "M T W TH F SA SU" printed thereon to identify each day of the week. The product may be provided with a sticker for the user to place onto the appropriate day of the week label on which the treatment regimen began, to serve as a reminder to alternate between the first and second treatment compositions every week on that particular day. In a related aspect, a system is provided comprising: the packaged skincare product and a server for sending notifications, over a network (e.g., a cellular, wireless, cable, internet, satellite, etc.), instructing a user of the packaged product as to which of said first or second skin treatment compositions to topically apply to said skin. The notifications may be sent daily or may be sent at least one day during said first period of time, and at least one day during said second period of time, for example, prior to the start of the next treatment modality. The server may also be configured to receive a start date for the treatment regimen from the user's computer. The system may further comprise a user's computer (e.g., smartphone, etc.) remote from the server for sending a start date to the server over a network, and receiving notifications from the server over the network.

These and other aspects of the present invention will be better understood by reference to the following detailed description and appended embodiments.

BRIEF DESCRIPTION OF THE DRAWINGS

FIG. 3 is a sample calendar of one embodiment of the invention showing a possible rotational regimen.

FIGS. 12A and 12B illustrate embodiments of the invention wherein two compositions are contained in separate reservoirs in a single container, where the container is marked with an alpha-numeric symbol identifying each reservoir (in this case, "1" and "2"). FIG. 12A also has an identifier indicating each day of the week visible on the container's exterior. FIG. 12B illustrates a variant of the embodiment of FIG. 12A in which a circular sticker has been placed on the day of the week on which the treatment regimen began (in this case, Monday or "M"). The packaging or label on the exterior of the container may have different colors or patterns or other visible images to identify reservoir 14 and 16 as indicated in FIGS. 12A and 12B by the different hatch marks.

DETAILED DESCRIPTION OF THE INVENTION

Figure 1:
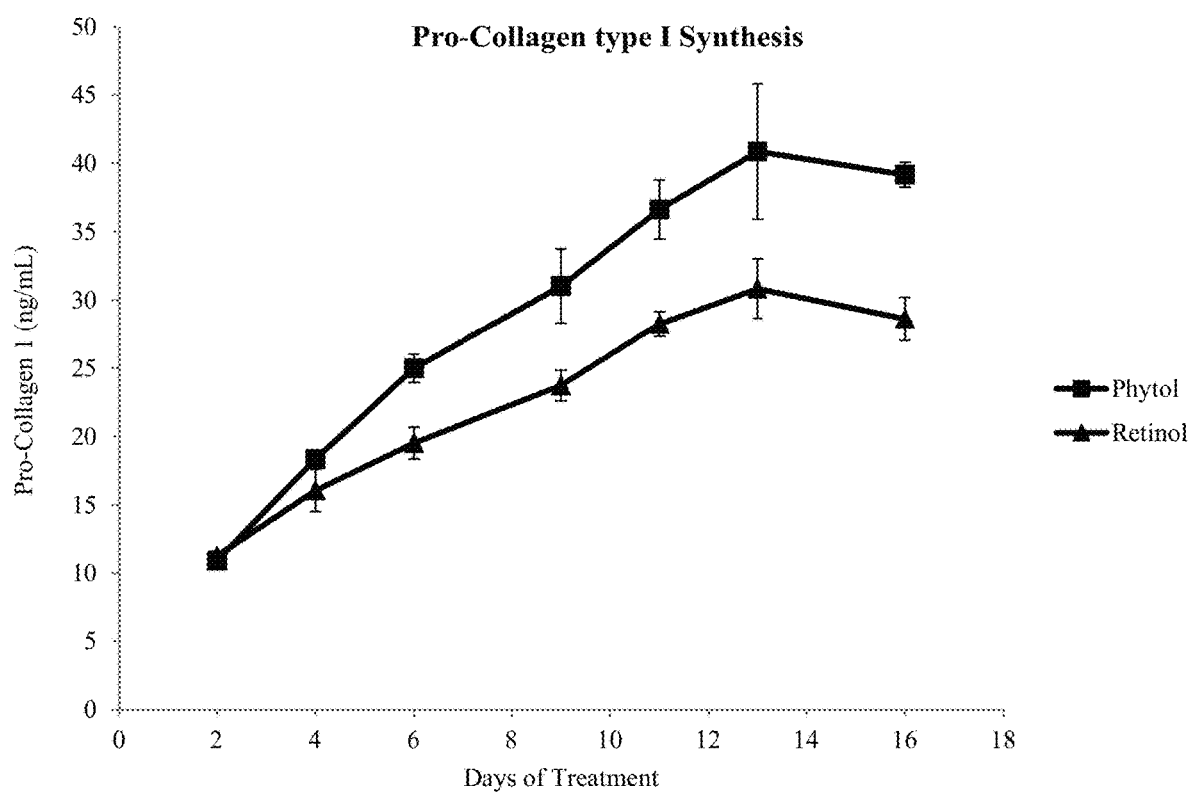
FIG. 1 is a plot of the amount of pro-collagen I as a function of treatment time in skin cells treated with (i) phytol alone (■), or (ii) retinol alone (▲) for 16 days. It is evident from FIG. 1 that retinol and phytol both plateau in effectiveness over time.

Detailed embodiments of the present invention are disclosed herein; however, it is to be understood that the disclosed embodiments are merely illustrative of the invention that may be embodied in various forms. In addition, each of the examples given in connection with the various embodiments of the invention is intended to be illustrative, and not restrictive. Therefore, specific structural and functional details disclosed herein are not to be interpreted as limiting, but merely as a representative basis for teaching one skilled in the art to variously employ the present invention.

All percentages given herein refer to the weight percentages of a particular component relative to the entire composition, including the vehicle, unless otherwise indicated. It will be understood that the sum of all weight % of individual components within a composition will not exceed 100%. Unless otherwise indicated, any ingredient (including active and inactive ingredients) may be included in a composition in an amount from about 0.0001-50% or from 0.001-20% or from 0.01-10% or from 0.1-5% by weight of the composition.

All terms used herein are intended to have their ordinary meaning unless otherwise provided. The phrase "physiologically acceptable" or "physiologically compatible" is used interchangeably with "cosmetically acceptable," "topically acceptable" and "dermatologically acceptable" and is intended to mean that a particular component is generally regarding as safe and non-toxic for application to a human integument (e.g., skin) at the levels employed.

The term "prevent," as used herein, includes delaying or slowing the onset of or progression of a particular sign of skin aging.

The phrase "individual in need thereof" refers to a human that could benefit from improved dermal appearance or health, including males or females. In some embodiments, the individual in need thereof is a female.

The term "skin" includes, without limitation, the lips, skin of the face, hands, arms, neck, scalp, and chest. As used herein, the term "consisting essentially of" is intended to limit the invention to the specified materials or steps and those that do not materially affect the basic and novel characteristics of the claimed invention, as understood from a reading of this specification.

The identification of a particular active agent as having a certain activity is not limiting, unless otherwise indicated, and does not preclude the same agent from having additional activities. For example, TDPA is listed herein as an "antioxidant," but it is also known to be a potent skin lightening agent. Likewise, hexylresorcinol also is identified herein as an "antioxidant," but it is also known to have antimicrobial, antiseptic and anesthetic activity, and is contemplated to be a skin lightening agent.

Reference to "$C_{2-20}$ esters" of active agents will be understood to include esters formed by $C_{2-20}$ hydrocarbon alcohols with carboxylic acid groups on the subject active agents or esters formed by $C_{2-20}$ hydrocarbon carboxylic acids with alcohol groups on the subject active agents. Likewise, "$C_{2-20}$ amides" of active agents will be understood to include amides formed by $C_{2-20}$ hydrocarbon amines with carboxylic acid groups on the subject active agents or amides formed by $C_{2-20}$ hydrocarbon carboxylic acids with amine groups on the subject active agents. The $C_{2-20}$ esters and amides, include, without limitation $C_{2-6}$ esters and amides, $C_{7-11}$ esters and amides, and $C_{12-20}$ esters and amides. The hydrocarbons may be aliphatic, aromatic, or partly aromatic and aliphatic. The hydrocarbons may be saturated, or contain one or more unsaturated (e.g., olefinic) bonds. In some embodiments, the $C_{2-20}$ esters or amides may be acetyl, propyl, lauryl, palmitate, palmitoyl, etc. In some embodiments, the "$C_{2-20}$ esters or amides" comprise a straight chain aliphatic $C_{16}$ hydrocarbon. The present invention embraces the use of all $C_{2-20}$ esters of all active agents described herein that have derivatizable hydroxyl or carboxylic acid functionalities. The invention also embraces the use of all $C_{2-20}$ amides of all active agents described herein that have derivatizable (i.e., reactive) amino or carboxylic acid functionalities.

The invention also embraces physiologically acceptable salts (e.g., acid addition salts, carboxylate salts, etc.) of any of the actives identified herein. The salts of the compounds that may be used according to the invention may be chosen from alkali metal or alkaline-earth metal salts or from zinc, magnesium or strontium salts, salts of an organic amine or quaternary ammonium salts. The salts of the compounds in accordance with the invention may be chosen from the salts of a mineral or organic acid, especially the hydrochlorides, hydrobromides or citrates.

In some embodiments of the present invention, at least two separate compositions are provided, each differing with respect to the identity or amount of at least one active ingredient. The active agent ("skincare active") will typically be dispersed or dissolved in a physiologically acceptable carrier (or diluent or vehicle). In various embodiments, any of the topical compositions of the invention (including the first and/or second, etc.) may comprise an effective amount of one of the following:

Retinoids, including Retinol and its $C_{2-36}$ esters (e.g., acetate, palmitate);

Ascorbic acid and its salts and $C_{2-36}$ esters (e.g., palmitate, tetrahexyldecyl, etc.)

Tocopherol and its $C_{2-36}$ esters (e.g., tocopherol acetate);

Glycolic acid and its salts (e.g., sodium or ammonium glycolate) or $C_{2-36}$ esters;

Lactic acid and its salts (sodium or ammonium lactate) or $C_{2-36}$ esters (e.g., myristyl);

Hexylresorcinol;

Niacinamide;

Thiodipropionic acid and its salts and $C_{2-36}$ esters (e.g., mono- and di-lauryl);

Phytol and its $C_{2-36}$ esters;

Peptides (e.g., hydrolyzed wheat gluten, hydrolyzed rice protein, Tetrapeptide-4, etc.)

Palmitoyl oligopeptides (e.g., Palmitoyl Tetrapeptides, Palmitoyl Pentapeptides, etc.)

Palmitoyl lysyl aminovaleroyl lysine (KavaK);

Ceramides (e.g., Ceramide-2);

L-4-Thiazolylalanine;

Cis-6-nonenol;

N-Acetyl amino acids (e.g., N-Acetyl Tyrosinamide);

Mesyloxybenzyl isobutylbenzenesulfonamide;

Cinnamido benzylpiperidinyl ethoxypropylbenzamide;

Caffeine;

Hyaluronic Acid and salts (e.g., Sodium Hyaluronate) and

Salicylic acid and derivatives (e.g., $C_{2-36}$ esters) thereof.

In some embodiments, the any of the compositions of the invention (e.g., the first, second, etc.) may comprise one or more of: Acetyl Hexapeptide-3, Acetyl Trifluoromethylphenyl Valyl-Glycine, Acetyl Tyrosinamide, Adenosine, Allantoin, All-Trans Retinoic Acid, Alpha Lipoic Acid, Alpha-Isomethyl Ionone, Amino Acids (Arginine, Glutamate, Glycine, Lysine, Etc.), Ammonium Glycolate, Apigenin, Arabinogalactan, Ascorbic Acid, Ascorbyl Glucoside, Ascorbyl Palmitate, Aspartic Acid, Astaxanthin, Atelocollagen, Azulene, Beta-Glucans, Bio-Flavonoids, Biosaccharide Gum-1, Biotin, Butylphenyl Methylpropional, Caffeine, Calcium Pantetheine Sulfonate, Calcium Pantothenate, Carnitine, Carnosine, Ceramide-2, Chlorphenesin, Cinnamido Benzylpiperidinyl Ethoxypropylbenzamide, Cis-6-Nonenol, Citral, Citronellol, Colloidal Platinum, Copper Peptides, Coumarin, Daidzein, DHT (Dihydrotestosterone or 5α-Dihydrotestosterone), Dilauryl Thiodipropionate, Dimethylethanolamine (DMEA), Disodium Stearoyl Glutamate, Dithiolane-3-Pentanic Acid, Ellagic Acid, Eugenol, Farnesyl Acetate, Ferrulic Acid and Derivatives (Ethyl Ferrulate, Sodium Ferrulate, etc.), Finasteride, Galactoarabinan, Gamma-Amino Butyric Acid (GABA), Genistein, Geraniol, Glucosamine, Glutamine, Glutathione, *Glycine Soja* Oil, Glycolic Acid, Hexamidine, Hexapeptide-2, Hexylrescorcinol, HGH Releasers, Hyaluronic Acid (HA) and salts, Hydrolyzed Rice Protein, Hydrolyzed Soy Protein, Hydrolyzed Wheat Gluten, Hydrolyzed Wheat Protein, Hydroquinone, Hydroxyethylpiperazine Ethane Sulfonic Acid, Hydroxyisohexyl 3-Cyclohexene Carboxaldehyde, 6-Hydroxy-2,5,7, Tetramethyl chroman-2-Carboxylic Acid, Idebenone, Isoeugenol, Latanoprost, Limonene, Linalool, Lysine Carboxymethyl Cisteinate, Tetrapeptides (e.g., Lys-Thr-Phe-Lys), Lysyl Aminovaleroyl Lysine, Magnesium Ascorbyl Phosphate, Malachite (antioxidant extract), Mesyloxybenzyl Isobutylbenzenesulfonamide, Minoxidil, N-Hydroxysuccinimide, Niacinamide, Nonenol, Oryzanol, Oxothiazolidinecarboxylic Acid, Palmitoyl Lysyl Aminovaleroyl Lysine (Kayak), Palmitoyl Oligopeptide, Palmitoyl Pentapeptide (Matrixyl), Palmitoyl Pentapeptide-3, Palmitoyl Pentapeptide-4, Palmitoyl Tetrapeptide, Palmitoyl Tetrapeptide-7, Palmitoyl Tetrapeptide-10, Panthenol, Panthetine Triacetate, Pentaerythrityl tetra-di-t-Butyl Hydroxyhydrocinnamate, Phloretin, Phytol, Phytosterols, *Pichia* Peptone Filtrate, Polyphenol Antioxidants, Propolis, Pycnogenol, Pyridoxine Hydrochloride, Quercetin, Resveratrol, Retinaldehyde, Retinoic Acid, Retinol, Retinyl Palmitate, Royal Jelly, Rutin, Saccharide Isomerate, Salicylic Acid, Salicyloyl Phytosphingosine, Sodium Chondroitin Sulfate, Sodium Hyaluronate, Soil Minerals, Sphingolipids, Sphingosine, Sugar Amines, Superoxide Dismutase, Tetrahexydecyl Ascorbate, Tetrapeptide-4, Thiazolylalanine, Thiodipropionic Acid, Tocopherol, Tocopheryl Acetate, Tretinoin, Trioxaundecanedioic Acid, Ubiquinone (Co Q10), Vitamin A, Vitamin B3, Vitamin E (Tocopherol), Xymenynic Acid, Zinc, and Zinc Pyrithione.

In some embodiments, one composition comprises a $C_{20}$-$C_{25}$ terpene alcohol (e.g., phytol) or a metalobilte thereof formed in human tissues (e.g., phytanic acid). In some embodiments, one composition comprises a retinoid (e.g., vitamin A, retinol, retinyl acetate, retinyl, propionate, reintyl palmitate, rentin-A, retinoic acid, retinaldyhyde, etc.).

In some embodiments, the first and second compositions will differ with respect to the presence of or amount of at least one active component. In some embodiments, however, the first and second compositions may comprise the same amount of an active agent, provided there are other differences between them (e.g., differences in the identity or amount of another active agent.

In some embodiments, at least one composition (e.g., the first composition) may comprise retinol (or an ester), and the second composition may either be free or essentially free of retinol (or an ester), by which is mean it comprises less than an effective amount, or comprise an amount of retinol (or an ester) that is more or less than the amount contained in the first composition.

The two different compositions form the bases of two different treatment modalities, each being carried out for a limited period of time, typically a predetermined period of time, after which the other treatment is carried out for a limited, typically predetermined, period of time. This process can be repeated any number of times to improve the health and appearance of human skin, while ideally overcoming or diminishing the impact of the sensitization or tolerance phenomenon that develops with skincare active, including retinoids and/or phytol treatment. The process may also be implemented with three, four, five, six, or seven (or more) different compositions in a like manner.

Without wishing to be bound by any theory, it is believed that methods according to some embodiments of the present invention provide multiple skin care benefits by activating retinoid X receptors (RXRs), peroxisome proliferator activated receptor (PPAR), and/or retinoic acid receptors RARs. Activating these receptors and responsive genes stimulates cell functions in multiple components of skin, such as the epidermis, dermis, sebaceous glands, melanocytes, Langerhan cells, and hair follicles while the alternating application allows skin resensitization. In some embodiments, the active agents, including a retinoid (e.g., retinol) and a $C_{20}$-$C_{25}$ terpene alcohol (e.g., phytol) or a metalobilte thereof formed in human tissues (e.g., phytanic acid), share at least one common mechanism of action, including, without limitation, activity at RXRs, PPARs, and/or RARs.

Phytol and its derivatives (e.g., $C_{1-20}$ ethers and esters) belong to the class of compounds which can be referred to as $C_{20}$-$C_{25}$ terpene alcohols. The phytol derivatives of the invention may comply with the structural formulas provided in WO 2001/066080 and U.S. Pat. No. 7,960,437, the disclosures of which is hereby incorporated by reference. Phytanic acid is also contemplated to be a useful phtyol derivative. Suitable phytol derivatives include, without limitation, $C_{1-20}$ hydrocarbon esters from the esterification of phytol with a $C_{1-20}$ carboxylic acid, or $C_{1-20}$ hydrocarbon esters from the esterification of phytanic acid with a $C_{1-20}$ hydrocarbon alcohol. The invention encompasses the use of phytol, as well as phytol derivatives (esters, ethers, etc.), phytol precursors, and phytol metabolites (including phytanic acid). Metabolic precursors of phytol are compounds from which phytol can be formed by action of enzymes present in human tissues, particularly skin. Metabolites of phytol are compounds formed by action of enzymes present in human tissues, particularly skin, on phytol.

In some embodiments, a composition of the present invention will comprise phytol, for example in an amount about 0.001 percent by weight (wt %) to about 10 wt % based on the total weight of the composition. Typically, phytol may be present in an amount about 0.01 wt % to about 5 wt %, and most typically about 0.1 wt % to about 1 wt %, based on the total weight of the composition.

The term "retinoid" includes: (1) retinol; (2) esters of retinol with carboxylic acids of 1 to 24 carbon atoms, such as retinyl acetate, retinyl propionate, retinyl butyrate, retinyl octanoate, retinyl laurate, retinyl palmitate, retinyl oleate, retinyl linoleate, and the like; (3) esters of retinol having an alpha-hydroxy carboxylic acid; (4) ether derivatives of retinol, including $C_{1-24}$ alkyl ether, ethers derived from glycolic acid, as well as glycolate ester and amide, such as retinyl glycolyl ether; (5) retinaldehyde; (6) retinoic acid; (7) esters of retinoic acid with alcohols of 1 to 24 carbon atoms; (8) isotretinoin as well as synthetic retinoid mimics, and derivatives of the foregoing, as well as others that bind to RAR receptors; (9) cis- and trans-isomers of the foregoing retinoids; (10) salts of the foregoing retinoids; and (11) mixtures of the any of the foregoing compounds. A preferred retinoid for use in a composition according to the present invention is retinol, including the cis- or trans-isomer of retinol, typically the trans isomer.

In some embodiments, a composition of the invention may comprise a retinoid (e.g., retinol) in an amount about 0.001 wt % to about 10 wt % based on the total weight of the composition. Typically, the retinoid (e.g., retinol) is present in an amount about 0.01 wt % to about 5 wt %, or about 0.1 wt % to about 2.5 wt %, based on the total weight of the composition. The amount of retinoid may be adjusted, based upon the potency of the retinoid, without departing from the present invention.

The invention provides methods that improve and/or support the health of skin and/or improve the appearance of one or more signs of dermatological aging when topically applied to human integuments (skin, lips, nails, hair, etc.), particularly skin, such as skin of the face. In some embodiments, at least two separate compositions, in which one composition has an antioxidant, such as a $C_{20}$-$C_{25}$ terpene alcohol (e.g., phytol), and the other composition has a different skincare active, such as a retinoid (e.g., retinol), are topically applied to the same area of skin in a sequential, rotating, or alternating fashion.

The two or more treatment modalities will typically comprise: (1) topical application (typically, at least once daily) of a first composition comprising a first active ingredient for a first period of time, and (2) topical application (typically, at least once daily) of a second composition comprising a second active ingredient for a second period of time, and (3) optionally repeating steps (1) and (2) one or more times. The first and second compositions may comprise at least one active ingredient that is different from the other, or is present in a different amount. In some embodiments, the first composition comprises phytol. In some embodiments, the second composition comprises phytol. In some embodiments, the first composition comprises retinol. In some embodiments, the second composition comprises retinol. In some embodiments, the first composition comprises phytol and the second composition does not comprise phytol or comprises phytol in a lesser amount than the first composition. In some embodiments, the first composition comprises retinol and the second composition does not comprise retinol or comprises retinol in a lesser amount than the first composition. In some embodiments, the second composition comprises phytol and the first composition does not comprise phytol or comprises phytol in a lesser amount than the second composition. In some embodiments, the second composition comprises retinol and the first composition does not comprise retinol or comprises retinol in a lesser amount than the second composition.

In some embodiments, the first composition is topically applied to the skin, at least once daily (e.g., once, twice or thrice daily, etc.) for a period of time from about 1-31 days (or from 1-5 days), or from about 3-20 days, or from about 5-10 days, or for about one week. In some embodiments, the second composition is topically applied to the same area of skin, at least once daily (e.g., once, twice or thrice daily, etc.) for a period of time from about 1-31 days (or from 1-5 days), or from about 3-20 days, or from about 5-10 days, or for about one week. In some embodiments, treatment with the second composition will begin after a predetermined time following the end of the first period of time, including, on the following day, or after two, three or more days (e.g., after five days, or one week), during which time the individual may optionally receive no treatment or may receive a treatment other than with the first and second compositions. In some embodiments, treatment with the first composition will begin after a predetermined time following the end of the second period of time, including, one the following day, or after two, three or more days (e.g., after one week), during which time the individual may optionally receive no treatment or may receive a treatment other than with the first and second compositions. In some embodiments, treatment with the second composition will begin on the day following the end of the first period of time. In some embodiments, treatment with the first composition will begin on the day following the end of the second period of time. In various embodiments, the treatment protocol will comprise the following: AB, ABA, ABAB, ABABA, or ABABAB, etc. In various embodiments, the treatment protocol will comprise the following: BA, BAB, BABA, BABAB, BABABA, etc., where "A" represents the first treatment period with the first composition and "B" represents the second treatment period with the second composition. The treatments may be continued until a skin benefit is observed or longer. The treatment protocol may be represented as $(AB)_{n+1}$ or $(BA)_{n+1}$, where "n" is an integer indicating the number of times the method is repeated. For example, "n" may be 1, 2, 3, and so on, up to 100 or more. Referring now to FIG. 3, a schedule for a possible first treatment period "A" and a second treatment period "B" is shown. In this embodiment, treatment period "A" is 7 days long and treatment period "B" is 7 days long. In another embodiment, treatment period "A" is 5 days long and treatment period "B" is 2 days long.

In some embodiments of the invention, a third treatment modality, such as topical application of a composition comprising an active agent different from said first and second compositions, may also be employed in sequence with the first and second treatment modalities. The third composition may be applied at least once daily for a third period of time according to the criteria described above. In various embodiments, the treatment protocol will comprises the following: ABC, ABCA, ABCAB, ABCABC, etc. and all permutations thereof, where "A" represents the first treatment period with the first treatment modality, "B" represents the second treatment period with the second treatment modality, and "C" represents the third treatment protocol with the third treatment modality. There is essentially no limit to the number of treatment modalities that may be employed, or the combination/permutation of orders in which these treatment modalities are employed. For example, the treatment may comprise two, three, four, five, six, seven or more different treatments, where each is typically employed at least once per day for a period from 1-31 days.

In some embodiments, any of the compositions of the invention may comprise any active for treating human skin. In some embodiments, any composition of the invention may be free of any active for treating human skin that is present in another of the compositions of the invention. In some embodiments, any of the compositions may include (or may be free of) an active ingredient selected from glycolic acid (and salts thereof), thiodipropionic acid (TDPA) or esters thereof (e.g., mono- and di-lauryl alcohol esters), hexylrecorcinol, niacinamide, or a botanical extract from a plants of the genus *Eclipta* (e.g., *Eclipta prostrata*), *Portulaca* (e.g., *Portulaca grandiflora*), *Tiliacora* (e.g., *Tiliacora triandra*) or *Melicope* (e.g., *Melicope hayesii* and/or *Melicope ellyarana*), etc. In some embodiments, the active ingredient will activate retinoid X receptors (RXRs), peroxisome proliferator activated receptor (PPAR), and/or retinoic acid receptors RARs. In some embodiments, the active ingredient will not activate retinoid X receptors (RXRs), peroxisome proliferator activated receptor (PPAR), and/or retinoic acid receptors RARs.

In some embodiments, the compositions of the invention (e.g., the first and/or second compositions, etc.) will comprise a biological extract. The extract may be an extract of a plant, yeast, fungus, etc. The extract may be from the roots and/or arial portions of a plant, including, without limitation, the stems, branches, bark, leaves, flowers, seeds, roots, fruit, rhizomes, vines, etc. Other biological materials, such as honeys may also be useful. Extracts include ground or pulverized plant materials, as well as ferments, lysates, and isolates. Without limiting the invention, extracts from the following are contemplated to be useful:

*Abies pindrow, Abrus fruticulosus, Abutilon indicum,* Acai, *Acacia catechu, Acacia dealbata, Acacia melanoxylon, Acer Saccharinum, Acer Saccharum* (Sugar Maple), acidopholus, *aesculus, Aesculus hippocastanum* (horse chestnut) seed, *Aframomum melegueata, agaricus,* agave, agrimonia, algae, *Alisma orientale, Allamanda cathartica,* almond, aloe, *Aloe barbadensis* leaf juice, *Alpinia galanga* leaf, *Amomum melegueta*, *Amorphophallus campanulatus* (rhizome/root), *Ananas sativus* (pineapple) fruit, *Anogeissus latifolia*, *Anthemis nobilis* (flower), *Antidesma bunis*, Apple extract, Apricot kernel, *Aradirachta indica*, *Archidendron clypearia*, *Arctostaphylos viscida*, *Argania spinosa*, *Argania spinosa* kernel, *Aribodopsis Thaliana*, *Arnica* flower, *Ascophyllum Nodosum*, *Asmunda japonica*, *Asparagopsis*, *Atriplex portulacoides*, *Averrhoa carambola*, *Azadirachta indica* (Neem), *Basella alba*, bearberry, bearberry extract, *Berchemia lineata* (leaf), *Beta vulgaris*, *Bifida Ferment* lysate, birch bark extract, Bitter orange flower, black cohosh (*Cimicifuga racemosa*), Black honey, Black Tea Ferment, *Boswellia serrata*, brassica, *Brassica Napus*, *Breynia fruticosa*, *Bupleurum falcatum* root, *Butea frondosa*, *Butea monosperma*, *Butyrospermum Parkii* Butter, *Caesalpinia sappan Linn*, *Calatropis gigantean*, *Calendula officinalis*, *Callistephus chinensis*, *Calotropis gigantea*, *Camelina sativa*, *Camellia oleifera* leaf, *Camellia sinensis* leaf, *Cananga odorata*, *Capsicum amuum*, *Capsicum frutescens* oleoresin, *Carica papaya* (*papaya*) fruit, Carrot, cashew, *Castanea sativa*, *Cayratia japonica*, cedar, *Cedrelopsis grevei*, *Cedrus deodara*, *Celosia argentea*, *Centella asiatica*, *Ceratonia siliqua* (carob), *Cereus grandiflorus* (cactus) flower, *Chalara microspora*, chamomile, *Chamomilla recutita* (*matricaria*) flower, Chestnut seed, *Chlorella vulgaris*, *Chondrus crispus*, *Cimicifuga racemosa* root, cinnamon, *Cistanche tubulosa*, *Cistus ladaniferus* L., Citronella, *Citrus aurantium*, *Citrus aurantium dulcis* (Orange) Fruit, *Citrus aurantium dulcis* peel, *Citrus Limon* (Lemon) Fruit, *Citrus Medica Limonum*, *Citrus Reticulata* Peel, *Clerodendron fragrans*, *Clerodendron lindleyi*, *Clerodendrum floribundum*, *Clinacanthus nutans*, *Clintonia borealis*, *Clitoria ternatea Linn* extract, Clove flower, *Coccinia grandis*, *Cocculus glaucescens*, *Cocos nucifera* (coconut) fruit juice, *Coffea arabica* (coffee) seed, cola, *Cola nitida* seed, comfrey, *Coleus forskohlii*, *Commersonia bartramia*, *Commiphom*, *Copernicia cerifera cera*, *Corallina officinalis*, *Crataegus monogyna* fruit, *Crithmum maritimum*, crocus flower, Cucumber fruit, *Cucumis sativus* (cucumber) fruit, *Curcuma longa*, *Curcuma Xanthorrhiza*, *Cymbopogon flexuosus*, *Cymbopogon nardus*, *Daucus carota sativa* (carrot) root, *Dendranthema indicum*, *Derris scandens*, *Desmanthus illinoensis*, *Dianella ensifolia*, *Dodonaea petiolaris*, *Dodonaea viscosa*, *Duboisia myoporoides*, *Eclipta prostrata*, *Edelweiss*, *Ehretia acuminate*, *Emblica officinalis*, English lavender, *Eperua falcata* bark, *Equisetum arvense*, *Equisetum Arvense* (Horsetail), *Eremophila mitchelli*, *Erthrina flabelliformis*, *Erythina indica*, *Erythrina flabelliformis*, *Erythrina indica*, *Eugenia caryophyllus* flower, *Eurya groffii*, Evening primrose oil, *Evernia furfuracea*, *Evernia prunastri*, *Eysenhardtia polistachya* (Palo Azul) wood, *Fagus sylvatica*, fenugreek seed, *Fibraretinum resica Pierre*, *Ficus benghalensis*, *Ficus coronata*, fir needle (*Abies alba*), *Foeniculum vulgare* (fennel) fruit, *forskohlii*, *Fructus Mume*, Geranium, *Ginkgo biloba*, *Glochidium wallichianum*, *Glycine soja* (soybean), *Glycyrrhiza glabra*, *Gomphrena globosa Linn*, *Goodenia ovata*, *Gracilaria textorii*, green tea, *Grifola frondosa*, *Gymnostemma pentaphyllum*, *Gynandropsis gynandra*, *Haberlea rhodopensis*, *Hamamelis viginiana*, hawthorns, *Hedyotis hedyotidea*, *Helianthus Annuus*, *Helianthus annuus* (sunflower) seed, *Helichrysum gymnocephalum*, *Helichrysum odoratissimum*, *Heliotropium indicum*, hibiscus flower, *Hibiscus sabdriffa*, holly (*Ilex*), honey, *Hordeum vulgare*, *Hoya carnosa*, *Humulus japonicus*, *Humulus Lupulus*, *Humulus scandens*, Hydrolyzed hibiscus esculentus, Hydrolyzed ulva lactuca, *Hymenosporum flavum*, *Hypericum performatum*, *Ilex paraguariensis* leaf, *Ilex purpurea Hassk*, *Innula racemosa*, *Ixora chinensis*, Japanese knotweed, *Jasminum officinale*, *Jasminum sambac* extract, Jojoba seed, *Jugans regia*, *Juniperus oxycedrus*, *Justicia ventricosa*, *Kunzea ambigua*, laurel clock vine (*Thunbergia laurifloria*), Lavandin, *Lavandula angustifolia* (Lavender), *Lavandula hybrida*, *Lavatera plebeian*, Lavender, *Lens esculenta* seed, *Lentinus edodes*, *Leptospermum lanigerum*, Licorice, *Ligusticum chiangxiong*, *Ligusticum lucidum*, locorice, *Lonchocarpus capassa*, *Loropetalum chinense*, *Lycium barbarium* (tibetan wolfberry), *Macrocyctis pyrifera*, *Maesa japonica*, *Mallotus philippinensis*, *Malus domestica* fruit cell culture, *Mammea siamensis*, Manuka Honey, Marjoram (leaf), *Matricarria* (flower), *Medemia nobilis*, *Medicago sativa* (alfalfa), *Melaleuca quinquernervia*, *Melicope hayesii*, *Melicpoe ellyarana*, *Melissa officinalis*, *Melissa officinalis* (leaf), *Menyanthes trifoliata*, *Mimosa tenuiflora* bark, *Mimusops elengi*, *Morinda citrifolia*, *Moringa oleifera*, *Moringa pterygosperma*, *Morus Nigra*, mucor miehei mushroom, MycoFusions *Coriolus* Black Corn Biomass, MycoFusions Maitake Waxy Hulless Barley Biomass, *Narcissus tarzetta*, *Naringi crenulata*, *Nerium indicum*, *Nigella sativa* (seed), Norway spruce, *Oenothera biennis* oil, *Olea europaea* (olive) (leaf), *Olisma orientale* extract, olive, *Omolanthes populifolius*, *Operculina turpethum*, *Ophiopogon Thunb.* P.E., Orange peel, *Origanum heracleoticum* flower, *Origanum majorana* (leaf), *Orthosiphon grandiflorus*, *Oryza* (rice) *sativa*, *Ozothamnus obcordatus*, *Padina pavonica*, palm nut, *Palmaria palmata*, *Panax ginseng* root, *Pancratium maritimum*, *Passiflora edulis* (seed), *Passiflora incarnata* flower, pecan, *Pelargonium graveolens* flower, *Pelvetia canaliculata*, *Perilla*, *Perilla ocymoides* (seed) oil, *Phaeodactylum tricornutum*, *Phyllanthus acidus*, *Phyllanthus emblica* fruit, *Phyllarthron bojeranum*, *Physalis minima*, pine needles, *Piper betel*, *Piper nigrum*, *Pisum sativum* (Pea), plankton, *Plumbago indica*, *Plumeria acuminata*, *Polyanthes tuberosa*, *Polygonum Cuspidatum*, Pomegranate, *Populus nigra*, *Portulaca oleracea*, *Portulaca sativa*, *Pouzolzia pentandra*, *Prunus amygdalus dulcis* (sweet almond) seed, *Prunus armeniaca* (kernel), *Psoralea corylifolia*, *Pteris semipinnata*, *Pueraria lobata* symbiosome, *Punica granatum* fruit, *Pygeum* (*Prunus*) *africanum*, *Pyrus malus*, *Pyrus malus* (apple) root, *Radix platycodonis*, *Raphia farinifera*, *Rhinacanthus nasutus*, *Rhizophora* mangle Bark, Rice bran oil, Roman chamomile, *Rosa canina* fruit, Rose flower, Rosemary (leaf), *Rosmarinus officinalis*, Royal jelly, *Rubis*, *Rubus ideas* (rasberry extract), *Rumex crispus*, *Saccharomyces cerevisiae*, *Saccharum officinarum* (Sugar Cane), *Salix nigra*, *Salvia officinalis*, *Salvia Sclarea*, *Sambucus chinensis*, *Sapindus rarak* (fruit), *Sargassum muticum*, *Sativa* bran oil, *Saxifraga sarmentosa*, *Scenedesmus*, *Scoparis dulcis*, *Scutellaria baicalensis* root, Sea Buckthorn, *Sedum sarmentosum* bunge, Seewead, *Selaginella tamariscina*, *Serrisa japonica*, *Sesbania aculeata*, *Sesbania grandiflora* (flower), *Siegesbeckia orientalis*, silver birch bark extract, *Silybum marianum* (fruit), *Simmondsia chinensis*, *Sophora tomentosa*, spruce needles, *Stellaria medica* (L.) cry., *Stenoloma chusana*, *Stephania rotunda*, *Stephania* solid, Sunflower seed, *Symphytum officinale*, *Tagetes erecta Linn*, *Terminalia bellerica*, *Tetracera asiatica*, *Theobroma cacao*, *Thermus thermophillus* ferment, *Thermus thermophilus*, *Thuja*, *Thunbergia laurifolia*, *Tilia cordata* wood, *Tilia platyphyllos*, *Tiliacora triandra*, tomato glycolipid, *Trifolium hybridum*, *Triticum vulgare* (wheat) germ, Turmeric root, *Uncaria gambir*, *Vaccinium macrocarpon* (Cranberry), *Vaccinium myrtillus* Fruit/Leaf *Vernonia*

*cinerea, Vigna aconitifolia, Vitis vinifera* (grape) fruit, Voandzeia substerranea, walnut, Water Lily, Willow (bark), *Withania somniferia*, yohimbine, *Zanthoxylum nitidium, Zea mays* (corn) kernel, and *Zingiber cassumunar* Roxb.

In the above list of biological/botanical extracts, the part of the plant indicated in parentheticals or otherwise represents a non-limiting embodiment. It will be understood that the invention encompasses extracts from any portion of the forgoing plants and organisms. In addition, the particular species indicated are also merely representative of certain embodiments, and in each instance the invention embraces extracts from any species within the genus. In other words, disclosure of *Melicope hayesii*, for example, will be understood to include extracts from the species *Melicope hayesii*, as well as extracts from any species within the genus *Melicope*.

The extracts may be prepared by solvent extraction, steam distillation, or any other method known in the art. In some embodiments, at least one of the topical compositions of the invention comprises an extract, obtained by steam distillation, of any of the forgoing plants and biological materials (each one being considered a distinct embodiment). In some embodiments, at least one of the topical compositions of the invention comprises an extract, obtained by extraction with water (e.g., basic, neutral, or acid), of any of the forgoing plants and biological materials (each one being considered a distinct embodiment). The water of extraction may further include a co-solvent miscible with water, including lower alcohols (e.g., C1-6), such as methanol, ethanol, isopropanol, propanol, butanol, etc. (typically, ethanol). In some embodiments, at least one of the topical compositions of the invention comprises an extract, obtained by extraction with a solvent system comprising from about 5-95% (v/v) or 10-90% (v/v) or 20-80% (v/v) or 40-60% (v/v) water (e.g., basic, neutral, or acid) and about 5-95% (v/v) or 10-90% (v/v) or 20-80% (v/v) or 40-60% (v/v) ethanol, of any of the forgoing plants and biological materials (each one being considered a distinct embodiment). In some embodiments, at least one of the topical compositions of the invention comprises an extract, obtained by extraction with an organic solvent (e.g., non-polar, polar aprotic, or polar protic), of any of the forgoing plants and biological materials (each one being considered a distinct embodiment). Suitable solvents include hexane and other $C_{1-12}$ or $C_{5-8}$ hydrocarbons, lower alcohols, $C_{2-16}$ ethers (e.g., diethyl ether), $C_{3-12}$ esters (e.g., ethyl acetate), $C_{2-12}$ (e.g., acetone, butanone, etc.), carbon dioxide (liquid or supercritical), etc. The biological extracts may be dried under vacuum or atmospheric pressure to remove water and solvents of extraction. The biological extracts may be dried by lyophilization. The biological extracts may be passed over activated carbon or charcoal and/or passed through filters and/or microfilters to remove bacteria and other biological materials.

Typically, the treatment regimen of the invention is repeated for a period of time sufficient to improve the health of skin and/or achieve a desired benefit of diminishing the signs of aging in the skin (e.g., reduction in number or severity of wrinkles and/or fine lines, or improving elasticity and/or diminishing sagging, etc.). This may entail treatment (e.g., topical application of compositions), at least once daily, for at least one week, or at least two weeks, or at least four weeks, or at least eight weeks or more. In some embodiments, the compositions are applied directly to a specific site of the skin (i.e., directly onto a wrinkle and/or fine line, under the eyes, on a blemish, etc.). In some embodiments, the first and/or second and/or third compositions will be applied to the skin in an amount from about 0.001 to about 100 mg/cm$^2$, more typically from about 0.01 to about 20 mg/cm$^2$, or from about 0.1 to about 10 mg/cm$^2$.

While the compositions and methods of the invention are contemplated to be useful for treating (i.e., reducing, ameliorating, improving, alleviating, forestalling, slowing, remediating and/or eliminating) the dermatological effects of aging (chronological, hormonal, or photo-aging) and/or environmental stress, they are also suitable for use in treating other dermatological conditions of the skin, including without limitation excessive or unwanted pigmentation. Numerous areas of the body can be treated, including, without limitation, the face, forehead, lips, scalp, neck, arms, hands, legs, knees, feet, chest, back, groin, buttocks, thighs, and the like. In some embodiments, the compositions are applied to the face, lips, chest, arms and/or hands, particularly, the face.

The cosmetically acceptable vehicle or carrier may be in the form of an emulsion. Non-limiting examples of suitable emulsions include water-in-oil emulsions, oil-in-water emulsions, silicone-in-water emulsions, water-in-silicone emulsions, wax-in-water emulsions, water-oil-water triple emulsions or the like having the appearance of a cream, gel or microemulsions. As used herein, the term "oil" includes silicone oils unless otherwise indicated. The emulsion may include an emulsifier, such as a nonionic, anionic or amphoteric surfactant, or a gellant, typically in an amount from about 0.001% to about 5% by weight.

The cosmetically acceptable vehicle may include water; vegetable oils; mineral oils; ester oils such as octal palmitate, isopropyl myristate and isopropyl palmitate; ethers such as dicapryl ether and dimethyl isosorbide; alcohols such as ethanol and isopropanol; fatty alcohols such as cetyl alcohol, cetearyl alcohol, stearyl alcohol and behenyl alcohol; isoparaffins such as isooctane, isododecane (IDD) and isohexadecane; silicone oils such as cyclomethicone, dimethicone, dimethicone cross-polymer, polysiloxanes and their derivatives, preferably organomodified derivatives including PDMS, dimethicone copolyol, dimethiconols, and amodimethiconols; hydrocarbon oils such as mineral oil, petrolatum, isoeicosane and polyolefins, e.g., (hydrogenated) polyisobutene; polyols such as propylene glycol, glycerin, butylene glycol, pentylene glycol, hexylene glycol, caprylyl glycol; waxes such as beeswax, carnauba, ozokerite, microcrystalline wax, polyethylene wax, and botanical waxes; or any combinations or mixtures of the foregoing. Aqueous vehicles, including serums, may include one or more solvents miscible with water, including lower alcohols, such as ethanol, isopropanol, and the like. The vehicle may comprise from about 25% to about 99.9% by weight of the composition.

In one embodiment of the invention, any of the compositions may include additional skin actives, including but not limited to, retinoids, botanicals, keratolytic agents, desquamating agents, keratinocyte proliferation enhancers, collagenase inhibitors, elastase inhibitors, 5-alpha reductase inhibitors, depigmenting agents, anti-inflammatory agents, steroids, anti-acne agents, antioxidants, and advanced glycation end-product (AGE) inhibitors, to name but a few. The amounts of these various ingredients are those conventionally used in the cosmetic field to achieve their intended purpose, and range individually or collectively typically from about 0.001 wt % to about 20 wt % by weight of the composition. The nature of these ingredients and their amounts must be compatible with the function of the compositions of the disclosure.

Exemplary anti-aging components include, without limitation, botanicals (e.g., *Butea frondosa* extract, *Tiliacora*

*triandra* extract, *Portulaca oleracea, Melicope elyarana*, etc.); hydroxy acids (including alpha-hydroxy acids and beta-hydroxy acids), salicylic acid and alkyl salicylates; exfoliating agents (e.g., glycolic acid, 3,6,9-trioxaundecanedioic acid, etc.), estrogen synthetase stimulating compounds (e.g., caffeine and derivatives); compounds capable of inhibiting 5 alpha-reductase activity (e.g., linolenic acid, linoleic acid, finasteride, and mixtures thereof); and barrier function enhancing agents (e.g., ceramides, glycerides, cholesterol and its esters, alpha-hydroxy and omega-hydroxy fatty acids and esters thereof, etc.), to name a few.

Exemplary retinoids include, without limitation, retinoic acid (e.g., all-trans, or 9-cis, or 13-cis), and derivatives thereof, retinaldehyde, retinol (Vitamin A) and esters thereof, such as retinyl palmitate, retinyl acetate and retinyl propionate, and salts thereof. Particular mention may be made of retinol. When present, the retinoids will typically be included in amounts from about 0.0001% to about 5% by weight, more typically from about 0.01% to about 2.5% by weight, or from about 0.1% to about 1.0% by weight. Compositions according to this embodiment will typically include an antioxidant such as ascorbic acid and/or BHT and/or a chelating agent such as EDTA or a salt thereof (e.g., disodium EDTA).

In another embodiment, the topical compositions of the present invention may also include one or more of the following: a skin penetration enhancer; an emollient, such as isopropyl myristate, petrolatum, volatile or non-volatile silicones oils (e.g., methicone, dimethicone), ester oils, mineral oils, and fatty acid esters; a humectant, such as glycerin, hexylene glycol or caprylyl glycol; a skin plumper, such as palmitoyl oligopeptide, collagen, collagen and/or glycosaminoglycan (GAG) enhancing agents; a sunscreen, such as avobenzone or octyl methoxycinnamate; an exfoliating agent; and an antioxidant.

Suitable tyrosinase inhibitors include thiodipropionic acid; hydroquinone; kojic acid; and others listed elsewhere in the instant application. Some skin lighteners or depigmenting agents, act as inhibitors of tyrosinase, an enzyme that has its catalytically active domain within organelles known as melanosomes. Tyrosinase converts phenols, including tyrosine, to ortho-quinones which are subsequently converted to melanin within the melanosomes.

Suitable melanin inhibitors include niacinamide serine-protease inhibitors; and others listed elsewhere in the instant application. These may act by disrupting the transfer of the melanosomes from melanocytes to the keratinocytes.

Suitable glycosaminoglycan (GAG) enhancing agents include, for example, phytol; terpene alcohols; peptides; PPAR modulators; and/or botanicals; and/or others listed elsewhere in the instant application. Glycosaminoglycans (GAGs) are produced by the body to maintain structural integrity in tissues and to maintain fluid balance. GAGs serve as a natural moisturizer and lubricant between epidermal cells to inhibit the production of matrix metalloproteinases (MMPs)—enzymes activated by UV exposure or inflammation that contribute to the breakdown of collagen while inhibiting new collagen formation. Topical GAG stimulants. GAG supplements and/or MMP inhibitors can help to provide temporary restoration of enzyme balance to slow or prevent matrix breakdown and consequent onset of wrinkle formation.

Suitable collagen enhancing agents include retinoids; peptides; botanicals; and others listed elsewhere in the instant application. Collagen and elastin are the major components of the dermal-epidermal junction (DEA i.e., a specialized structure mediating close contact between the lamina densa (the basement membrane zone between the epidermis and the dermis of the skin) and the underlying connective tissue of the dermis. The dermal-epidermal junction (DEJ) includes interlocking fingerlike projections called Rete ridges. The cells of the epidermis receive their nutrients and oxygen from the blood vessels in the dermis because the epidermis does not have its own blood vessels. The Rete ridges at the DEJ increase the surface area of the epidermis that is exposed to the dermis, so that the uptake of necessary nutrients/oxygen is more efficient, and the two layers of skin can bind more strongly and resist mechanical stress. The DEJ flattens out with aging, such that the skin is more fragile and more likely to shear. This process also decreases the amount of nutrients/oxygen available to the epidermis by decreasing the surface area of the epidermis in contact with the dermis, thereby interfering with the skin's normal repair process. As a result, the skin shows signs of aging such as fragility, lines and wrinkles, sagging, dull, discoloration, and uneven tone, rough texture, and the like. The main structural component of the dermis is also collagen. Bundles of collagen molecules pack together throughout the dermis, accounting for three-fourths of the dry weight of skin. Procollagen is the precursor molecule of collagen, synthesized in the fibroblast, osteoblast, etc., and cleaved to form collagen extracellularly. Collagen has great tensile strength, and along with soft keratin, is responsible for skin strength and elasticity. As aging occurs, the production of collagen is reduced, while the degradation is accelerated due to an overproduction of collagenase, i.e., protease that breaks down collagen. Collagen deficiency may lead to reduction in skin strength and elasticity, which in turn may lead to wrinkles, sagging, and fragility of the aging skin. For a more detailed background on collagen, see Lodish, et al. Molecular Cell Biology, W.H. FREEMAN, New York, N.Y. 4.sup.th edition, 2000. Thus, it is anticipated that, the retention of or stimulation of collagen and/or procollagen production and/or the reduction in production of collagenase would provide for a healthier and stronger skin, thereby reducing wrinkles, sagging, and fragility of the aging skin.

Suitable barrier enhancing agents include phytol, and ceramides, such as ceramide-2, glycerides, cholesterol and its esters, alpha- and omega-hydroxy fatty acids and esters thereof, etc.); and others listed elsewhere in the instant application.

Suitable anti-inflammatory agents include thiodipropionic acid; and others listed elsewhere in the instant application.

Suitable anti-cellulite agents (in one embodiment, intracellular triglyceride inhibitors) include *Coleus forskohlii*; CPT-1 modulators; starfruit extract; caffeine; and others listed elsewhere in the instant application. Cellulite is the lumpy uneven type of subcutaneous fat that tends to accumulate on the buttocks, thighs, and limbs of many women. It is considered unsightly because it gives the tissues underlying the skin an "orange peel" or "cottage cheese" look. Compressing the skin, as when sitting or crossing the legs, produces a "mattress appearance" with bulging and pitting of the fatty layer. Nodules of fat may be felt trapped within hardened connective tissue. The histology of cellulite-affected skin indicates that cellulite results from a combination of enlarged fat tissue and weak dermal structure and connective tissue septa. Excess fat accumulation increases the volume of adipocytes, which bulge into a weakened dermis to create the characteristic irregularities in the appearance of the epidermal surface. A number of factors can cause cellulite including, e.g., hereditary, intestinal, circulatory, lymphatic, hormonal, and lifestyle factors. Dieting to decrease fat intake, exercising to increase fat metabolism and prevent the build up of cellulite, and massage and hydrotherapy to stimulate lymphatic drainage can help reduce the appearance of cellulite. Nonetheless, these means for combating cellulite or subcutaneous fat are limited, and the need remains for additional approaches. The protrusion of enlarged fat tissue into the dermis is one of the major factors contributing to the appearance of cellulite. One of the approaches to improve cellulite is to stimulate fat breakdown and reduce the amount of fat and/or lipids in the adipocytes, or fat cells.

Suitable hydroxyl acids and derivatives thereof include sodium glycolate; oxa diacids; alpha-hydroxy acid; and others listed elsewhere in the instant application.

Suitable retinoids and derivatives thereof include retinol; and others listed elsewhere in the instant application.

Suitable antioxidants include thiodipropionic acid; and others listed elsewhere in the instant application.

Suitable vitamins include niacinamide; and others listed elsewhere in the instant application.

Suitable terpene alcohols include phytol; and others listed elsewhere in the instant application.

Suitable peptides include K-ava-K; KTFK; n-acetyl tyrosinamide; and others listed elsewhere in the instant application.

Suitable PPAR modulators include phytol and others listed elsewhere in the instant application.

Suitable botanicals include *Portulaca oleracea; Tiliacora triandara; Berchemia lineata*; and others listed elsewhere in the instant application.

Suitable exfoliating agents include, for example, alpha-hydroxy acids, beta-hydroxy acids, oxa-acids, oxadiacids, and their derivatives such as esters, anhydrides and salts thereof. Suitable hydroxy acids include, for example, glycolic acid, lactic acid, malic acid, tartaric acid, citric acid, 2-hydroxyalkanoic acid, mandelic acid, salicylic acid and derivatives thereof. One exemplary exfoliating agent is glycolic acid. When present, the exfoliating agent may comprise from about 0.001% to about 20% by weight of the composition.

Examples of antioxidants that may be used in the present compositions include compounds having phenolic hydroxy functions, such as ascorbic acid and its derivatives/esters; beta-carotene; catechins; curcumin; ferulic acid derivatives (e.g., ethyl ferulate, sodium ferulate); gallic acid derivatives (e.g., propyl gallate); lycopene; reductic acid; rosmarinic acid; tannic acid; tetrahydrocurcumin; tocopherol and its derivatives, including tocopheryl acetate; uric acid; or any mixtures thereof. Other suitable antioxidants are those that have one or more thiol functions (—SH), in either reduced or non-reduced form, such as glutathione, lipoic acid, thioglycolic acid, and other sulfhydryl compounds. The antioxidant may be inorganic, such as bisulfites, metabisulfites, sulfites, or other inorganic salts and acids containing sulfur. Antioxidants may comprise, individually or collectively, from about 0.001% to about 10% (w/w), or from about 0.01% to about 5% (w/w) of the total weight of the composition.

Other additives include: vitamins, such as tocopherol and ascorbic acid; vitamin derivatives such as ascorbyl monopalmitate, tocopheryl acetate, and Vitamin E palmitate; thickeners such as hydroxyalkyl cellulose, carboxymethylcellulose, carbombers, and vegetable gums such as xanthan gum; gelling agents, such as ester-terminated polyester amides; structuring agents; metal chelating agents such as EDTA or salts thereof; pigments; colorants; and pH adjusters (citric acid, ethanolamine, sodium hydroxide, etc.). The composition may optionally comprise other components known to those skilled in the art including, but not limited to, film formers, moisturizers, minerals, viscosity and/or rheology modifiers, anti-acne agents, insect repellents, skin cooling compounds, skin protectants, lubricants, fragrances, preservatives, stabilizers, and mixtures thereof. In addition to the foregoing, the cosmetic compositions of the invention may contain any other compound for the treatment of skin disorders.

In addition, the compositions contemplated by this disclosure can include one or more compatible cosmetically acceptable adjuvants commonly used and known by the skilled practitioner, such as colorants, pearls, chromalites, micas, pigments, dyes, fragrances, emollients, humectants, preservatives, vitamins, chelators, thickeners, anesthetics, anti-allergenics, antifungals, antimicrobials, other anti-inflammatory agents, antioxidants, antiseptics, depigmenting agents, film formers, insect repellents, pharmaceutical agents, photostabilizing agents, sunscreens, stabilizers, surfactants, thickeners, viscosity modifiers, and botanicals. The topical compositions of the present disclosure may also include a skin penetration enhancer, a surface smoother, a skin plumper, an optical diffuser, an exfoliation promoter, and an antioxidant. Details with respect to these and other suitable cosmetic ingredients can be found in the "International Cosmetic Ingredient Dictionary and Handbook," 10th Edition (2004), published by the Cosmetic, Toiletry, and Fragrance Association (CTFA), at pp. 2177-2299, which is herein incorporated by reference in its entirety. The amounts of these various substances are those that are conventionally used in the cosmetic or pharmaceutical fields, for example, they can constitute from about 0.01% to about 20% of the total weight of the composition.

A sunscreen may be included to protect the skin from damaging ultraviolet rays. In an illustrative embodiment of the present disclosure, the sunscreen provides both UVA and UVB protection, by using either a single sunscreen or a combination of sunscreens. Among the sunscreens that can be employed in the present compositions are avobenzone, cinnamic acid derivatives (such as octylmethoxy cinnamate), octyl salicylate, oxybenzone, octocrylene, titanium dioxide, zinc oxide, or any mixtures thereof. The sunscreen may be present from about 1 wt % to about 30 wt % of the total weight of the composition.

In one embodiment, the topical compositions will have a pH range from 1 to 13, with a pH in the range of from 2 to 12 being typical. In some embodiment, the composition will have a pH in the range of from 3.5 to 7 or from 7-10.5. In some embodiments, the pH will be in the range of 3-4, or 4-5, or 5-6, or 6-7, or 7-8, or 8-9, or 9-10, or 10-11, or 11-12. Suitable pH adjusters such as sodium hydroxide, citric acid and triethanolamine may be added to bring the pH within the desired range.

It will be understood that the foregoing optional active and inactive ingredient(s) may be included in one or all of the compositions according to the inventions (e.g., both the first and the second compositions).

Another embodiment of the present disclosure is directed to the delivery of the described compositions by the use of targeted delivery systems, for example, liposomes, injection, microspheres, (see, e.g., U.S. Pat. No. 5,770,222 to Unger et al.), and the like, so that the components and/or active constituents can more readily reach and affect the subcutaneous layer of the area of application, e.g., face or neck, or the other area of the skin.

The compositions may be formulated in a variety of product forms, such as, for example, a lotion, cream, serum, spray, aerosol, cake, ointment, essence, gel, paste, patch, pencil, towelette, mask, stick, foam, elixir, concentrate, and the like, particularly for topical administration. The compositions are typically formulated as a lotion, cream, ointment, or gel. The first and second compositions may also take difference forms from one another.

In certain embodiments of the invention, the compositions are applied topically to improve the appearance and/or health of human skin. The improvement in the appearance and/or health of human skin may be an improvement of any attribute or characteristic of skin, including without limitation:

(a) treatment, reduction, and/or prevention of fine lines or wrinkles;
(b) reduction of skin pore size;
(c) improvement in skin thickness, plumpness, and/or tautness;
(d) improvement in skin smoothness, suppleness and/or softness;
(e) improvement in skin tone, radiance, and/or clarity;
(f) improvement in procollagen, and/or collagen production;
(g) improvement in maintenance and remodeling of elastin;
(h) improvement in skin texture and/or promotion of retexturization;
(i) improvement in skin barrier repair and/or function;
(j) improvement in appearance of skin contours;
(k) restoration of skin luster and/or brightness;
(l) replenishment of essential nutrients and/or constituents in the skin;
(m) improvement of skin appearance decreased by aging and/or menopause;
(n) improvement in skin moisturization;
(o) increase in skin elasticity and/or resiliency;
(p) treatment, reduction, and/or prevention of skin sagging;
(q) improvement in skin firmness; and
(r) reduction of pigment spots and/or mottled skin; and
(s) improvement of optical properties of skin by light diffraction or reflection.

In some embodiments, the compositions are intended to treat wrinkles and/or fine lines in the skin, including forehead wrinkles, "crow's feet," and wrinkles at the edges of the eyes or mouth. In some embodiments, the compositions are applied directly to a wrinkle and/or fine line. The treatment may reduce the severity (e.g., depth) of the wrinkles and fine lines and/or may reduce the number of wrinkles and/or fine lines in a given area of skin. In some embodiments, the compositions are intended to treat sagging skin which may result from a loss of dermal elasticity. In this embodiment, the compositions may be applied to skin of the checks, jowls, etc.

It is also contemplated that the methods of the invention will be useful for treating thin skin by topically applying the composition to thin skin of an individual in need thereof. "Thin skin" is intended to include skin that is thinned due to chronological aging, menopause, or photo-damage and skin that is thinning prematurely. In some embodiments, the treatment is for thin skin in men, whereas other embodiments treat thin skin in women, pre-menopausal or post-menopausal, as it is believed that skin thins differently with age in men and women, and in particular in women at different stages of life.

The methods of the invention may be employed prophylactically to forestall aging including in individuals that have not manifested signs of skin aging, most commonly in individuals under 25 years of age. The methods may also reverse or treat signs of aging once manifested as is common in individuals over 25 years of age, or to slow the progression of dermatological aging in such individuals.

In certain embodiments, the cosmetic compositions described herein can be used to treat and/or prevent hyper-pigmentation of skin and/or of the hair, for example, to lighten skin or hair. In some embodiments, the compositions are topically applied to the skin or hair, for example to an area of hyper-pigmented skin or hair. Hyper-pigmentation includes any coloration of an individual's skin or hair that is darker than desired by the individual and that is caused by melanocytes. Such unwanted pigmentation may also be called discoloration. Hyper-pigmented areas of the skin include areas of discrete or mottled hyper-pigmentation. Areas of discrete hyper-pigmentation can be distinct, uniform areas of darker color and may appear as brown spots or freckles on the skin, including marks commonly called pigment spots or "age spots." Areas of mottled hyper-pigmentation of the skin can be dark blotches that are larger and more irregular in size and shape than areas of discrete pigmentation. Areas of hyper-pigmentation also include areas of tanned skin, for example, skin tanned due to UV exposure. Hyper-pigmented hair includes any shade of hair that is darker than desired.

Treating hyper-pigmentation or hyper-pigmented skin/hair refers to eradicating, reducing, ameliorating, or reversing one or more of the unwanted features associated with hyper-pigmentation, such as producing a perceptible lightening of the skin or hair in the affected area. Lightening hyper-pigmented areas of the skin may be desirable, in one embodiment, in diminishing age spots; lightening a suntan; evening or optimizing skin tones, e.g., in areas of mottled hyper-pigmentation; in treating melasmic and chloasmic patches, freckles, after-burn scars, and post-injury hyper-pigmentation. Preventing hyper-pigmentation or hyper-pigmented skin refers to affording skin, not yet affected by hyper-pigmentation, a benefit that serves to avoid, delay, forestall, or minimize one or more unwanted features associated with skin hyper-pigmentation, such as reducing the darkness or size of hyper-pigmented areas that eventually develop.

In one embodiment, the compositions of the invention are applied to human skin to reduce sebum production or improve the appearance of skin affected by cellulite, and/or reduce unwanted lipogenesis or increase lipolysis. In this embodiment, the terpene alcohols and/or retinoids can be formulated in cosmetically acceptable vehicles (as described herein) and may include one or more additional agents such as anti-acne ingredients (e.g., salicylic acid, benzoyl peroxide and other peroxides, sulfur, retinoids, etc.) in the case of a facial composition, or, in the case of a cellulite treatment, the formulation may comprise any ingredients suitable for treatment of cellulite, including without limitation, *Coleus forskohlii*, *perilla* oil and other unsaturated fatty oils and omega-3 fatty acids such as alpha-linolenic acid; conjugated linoleic acid (CLA); caffeine; theophylline; xanthines; retinoids (e.g., retinol); epigallocatechin gallate; and the like. A cellulite treatment composition according to the invention may comprise effective amounts of a lipolysis stimulator, lipogenesis inhibitor, or an adipogenesis inhibitor. The cellulite treatment may comprise a PPAR ligand, which may be an inhibitor of upregulation of any of the PPAR isoforms, such as PPAR-α and/or PPAR-γ. The cellulite treatment may comprise CPT-1 inhibitor, for example and extract of Star Fruit. A cellulite treatment according to the invention will typically be applied topically to skin suffering from cellulite, including skin of the buttocks and thighs for a period of time sufficient to improve the appearance thereof, including for example, daily treatment for at least four weeks, at least eight weeks, at least twelve weeks, or longer. In one embodiment, the compositions are topically applied to treat acne.

In one embodiment, the compositions are intended for use as a non-therapeutic treatment. In another embodiment, the compositions are articles intended to be rubbed, poured, sprinkled, or sprayed on, introduced into, or otherwise applied to the human body for cleansing, beautifying, promoting attractiveness, or altering the appearance, in accordance with the US FD&C Act, § 201(i).

In another embodiment, a kit and/or a method of periodic or rotational skincare treatment is contemplated. The kit may comprise: (i) a of a plurality of topical compositions comprising a physiologically acceptable vehicle; (ii) a second of a plurality of topical compositions comprising a physiologically acceptable vehicle, said first topical composition being physically separated from said second topical composition, and (iii) optionally, written instructions for topically applying said first and second topical compositions in alternating fashion, in any order, such that the first composition is applied at least once daily for a first period of time from 1-31 days and said second composition is applied at least once daily for a second period of time from 1-31 days.

In one embodiment, the plurality of compositions are each contained in a separate container as a single ingredient, wherein multiple single-formula containers (for example, jars and dispensers) are sold and/or packaged together.

In another embodiment, the plurality of compositions exist as different physical layers within the same container (for example, separated by density and/or miscibility of layers), which may be packaged in jars, dispensers, and/or other container types.

In another embodiment, the plurality of compositions are contained in different sachets that may themselves be packages and/or sold together, and that may be arrayed linearly; in a matrix; and/or radially.

In another embodiment, the plurality of compositions are contained in different bliser packs that may themselves be packaged and sold together, and that may be arrayed linearly; in a matrix; and/or radially.

In another embodiment, the plurality of compositions are contained in different reservoirs within the same package.

In another embodiment, the plurality of reservoirs each comprise a single dose of said first and second topical compositions, respectively.

In another embodiment, the plurality of reservoirs are not separable from one another.

In another embodiment, the plurality of reservoirs are marked with a plurality of different identifiers (e.g., color, symbol, light, display, QR code, etc.), respectively.

In another embodiment, an identifier (e.g. color, symbol, light, display, QR code, etc.) is utilized to indicate to the user to switch use from a first composition to a second composition and/or which composition to use on a given treatment opportunity. In another embodiment, the packaging contains an indicator light that indicates whether the user should apply the first composition or the second composition. In another embodiment, the first and/or second containers contain an electronic display that indicates whether the user should apply the first composition or the second composition.

In another embodiment, written instructions indicate to the user which treatment modality to use on a particular day by reference to the plurality of identifiers.

In another embodiment, the order of treatment modalities to use is stochaistic or randomly generated.

In another embodiment, the method or kit further includes a calendar, the calendar identifying a first time period comprising from 1-31 days, said first time period being marked with said first identifier, and a second time period comprising from 1-31 day, said second time period being marked with said second identifier. In another embodiment, the method or kit further includes written instructions (e.g., a QR code) for accessing a calendar over the Internet, wherein said calendar instructs the user whether to apply the first or second composition depending on the day. In one embodiment, the calendar will have, on each day, an indicator or symbol uniquely identifying one of the compositions, which may, for example, be packed in containers or reservoirs also identified by the same indicators or symbols.

In another embodiment, the method or kit further includes written instructions for accessing data over the Internet (e.g., a QR code), wherein the data (in, for example, the form of an algorithm or application or in the form of a text message or other data communication) provides the user with instruction as to which treatment modality to apply; and where the data may be accessible through a smartphone application, Website, etc.

In other embodiments, a system is provided comprising a skin care product and a server and optionally a computer remote from the server. The skin care product may be as described herein, and may, for example, have separated in different reservoirs within the same packaging or container, two different skin treatment compositions that may be independently dispensed from said packaging or container; and an indicator for distinguishing between said skin treatment compositions. The server is typically configured to receive, over a computer network, from a user of said skin care product, a date on which a skin treatment regimen is started, and configured to send, over a computer network, to said user a plurality of notifications on a plurality of different days instructing the user as to which of said first or second skin treatment compositions to topically apply to said skin. The skin care product may further comprise an identifier (e.g., alpha-numberic code, barcode, QR code, etc.) which is capable of identifying said skin treatment compositions, and the server may be configured to receive said identifier from the user in addition to a start date. Based on the identifier, the server may use information regarding first and second compositions in the particular product and the said start date to calculate the treatment regimen for the said first and second compositions. For example, the server may be instructed to use a particular value for the first period of time and particular value for the second period of time based on the identifier. The server may be configured to send, over a computer network, to said user a plurality of notifications on a plurality of different days instructing the user as to which of said first or second skin treatment compositions to topically apply to said skin, based on the user input of a start date and a predetermined duration of the first and second periods of time. The system may further comprise a computer remote from the server (e.g., cell phone, telephone, smart phone, tablet, wearable device, watch, pager, computer, laptop, etc.), under the control of the user, for sending the start date to said server and for receiving the plurality of notifications.

Figure 6:
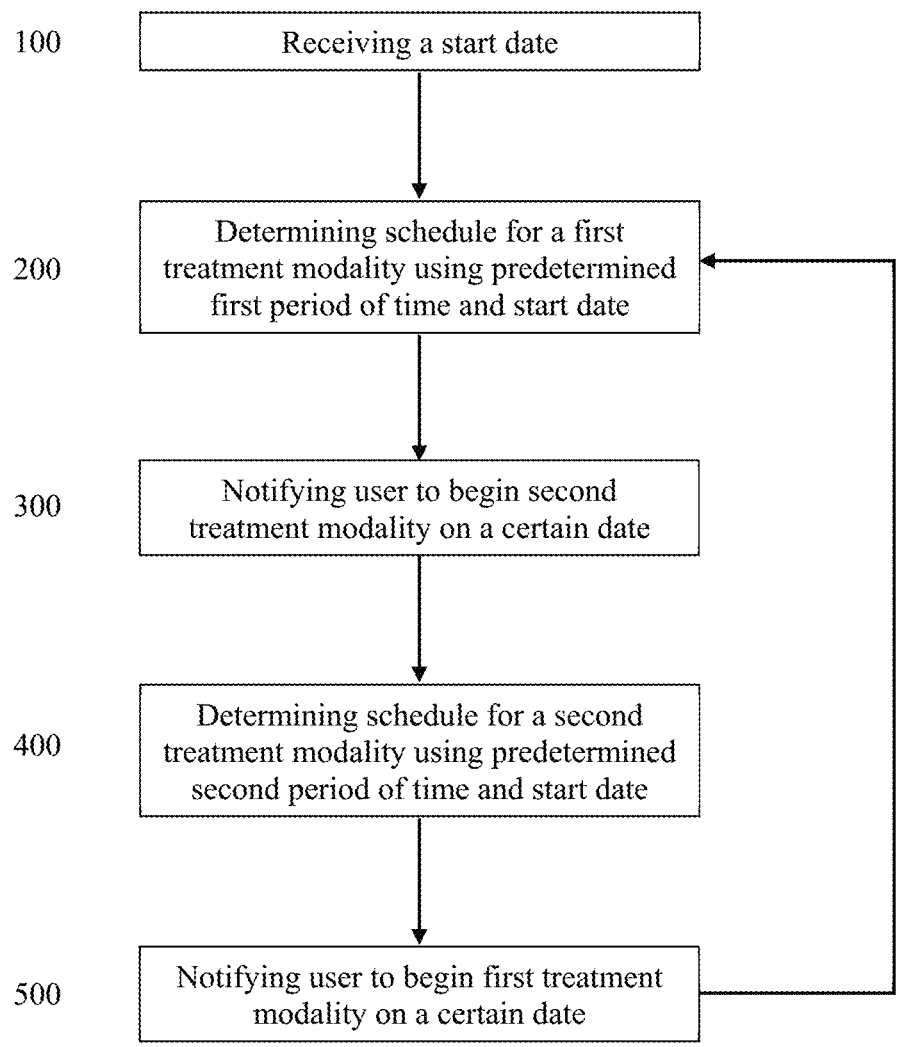
FIG. 6 is a flow chart of a method and system for notifying a user of a product according to the invention, which of two treatment compositions should be used on a particular day.

Referring now to FIG. 6, a flow chart illustrates the process and system in which a user, for example, via a computer (e.g., smartphone, laptop, desktop computer, etc.), sends a start date and said server receives said start date at step 100. The sending and receiving may occur over a network, such as the Internet, a wireless network, land lines, satellite, etc. Based on the start date, the server determines a schedule for the first treatment modality using the predetermined first period of time (typically from 1-31 days, or 2-15 days, or 7 days), at step 200. This may entail adding the first period of time to the start date. The user would apply a first composition from the product during this first period of time. The server may notify (e.g., by text message, email, social media post, telephone, etc.) the user one or more times (e.g., daily) during the first treatment time to apply the first composition on that day. Alternatively, the server may notify the user only when it is time to change the treatment to the second composition, e.g., prior to the end of, or at the end of, the first treatment period at step 300. The server may use the start date to determine an end date for the first treatment regimen, based on predetermined or user supplied input of a first treatment period of time. For example, the first treatment period may be seven days, which may be a predetermined instruction on said server or may be inputted or selected by the user. Prior to the end date of the first treatment modality, the server may calculate the start and end dates of a second treatment modality, again based on pre-determined input or based on user supplied input for the desired duration of the second treatment regimen at step 400. This may entail adding the first period of time and second period of time to the start date, or adding the second period of time to the value determined in step 200 (i.e., the end of the first treatment schedule). The server may notify the user prior to the end of, or at the end of, the second treatment regimen to begin the first treatment regimen on a certain date at step 500. The server may repeat steps 200-500 for any number of iterations, typically more than four. The number of iterations based on pre-determined input or based on user supplied input. On the second or any greater iteration, the server may repeat steps 200-500 based on the start date, the length of the first and second periods of time, and the iteration number. Alternatively, the server may send notifications of any first or second treatment modality during any previous first or second periods of time.

In another embodiment, the user may scan or image their treated integument, for example, using the camera of a smartphone, and send the scan or image to the server. The server may be configured to generate customized instructions on further treatment from Internet data or application, and send those instructions to the user's computer over the network.

In another embodiment, first and second compositions are contained in separate reservoirs within a single container, wherein the container has a first pump in fluid communication with the reservoir containing the first composition for dispensing said first composition and a second pump in fluid communication with the reservoir containing the second composition for dispensing said second composition, each pump optionally being disposed on opposite side of said container, and each pump optionally being covered by a removable cap such that the user removes the cap from one end while holding the cap that covers the other end.

Figure 7:
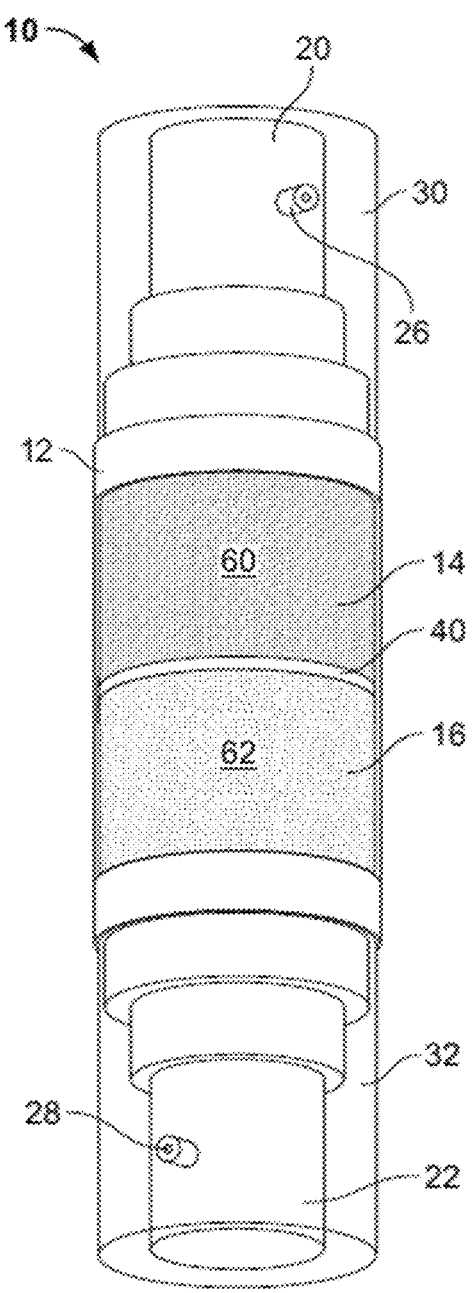
FIG. 7 and FIG. 8 are examples of another packaging embodiment of the invention having two reservoirs in a single container which are not separable from one another and which are each charged with a different skincare composition.
Figure 8:
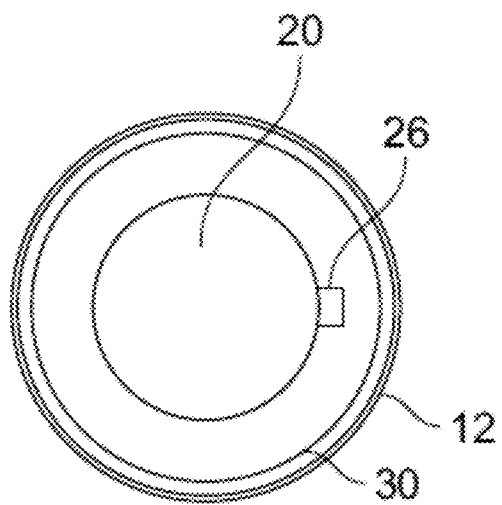
Figure 9:
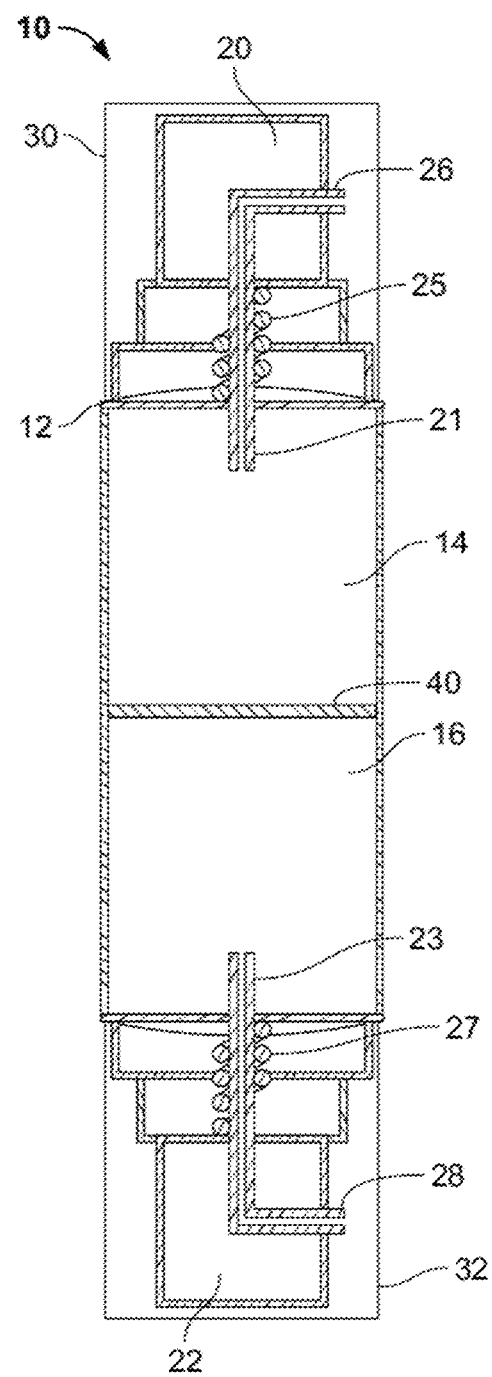
FIG. 9-11 are cross sectional views of a packaging embodiment of the invention illustrating operation of each pump to dispense a first cosmetic composition from the first reservoir using the first pump (FIG. 10) and dispensing a second cosmetic composition from a second reservoir using the second pump (FIG. 11).
Figure 10:
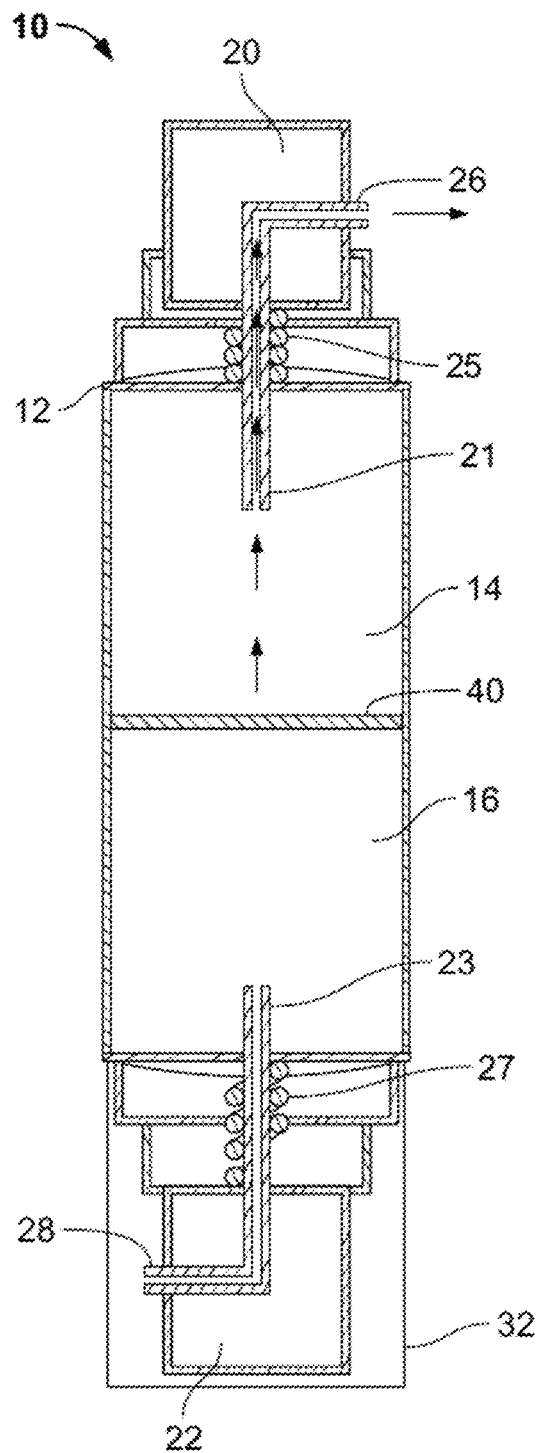
Figure 11:
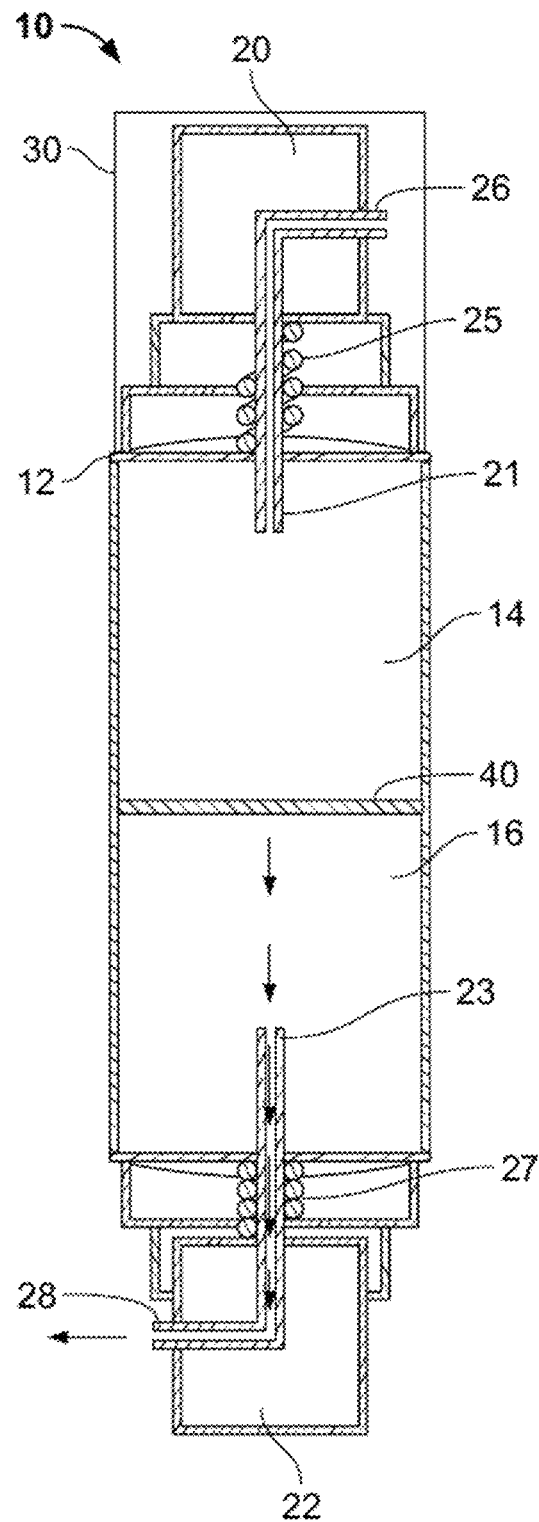
Figure 13:
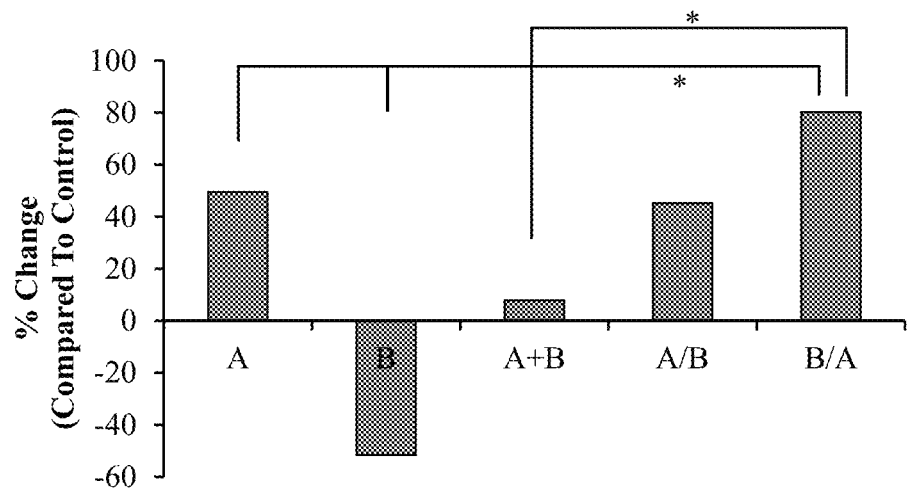
FIG. 13 is a plot of the percentage change from a control in the amount of hyaluronic acid produced in human dermal fibroblast when exposed to (A) a ten day treatment of hydroponic *Tiliacora triandra* extract, (B) a ten day treatment of niacinamide, (A+B) a ten day treatment of *Tiliacora triandra* and niacinamide, (B/A) a five day treatment of *Tiliacora triandra* followed by a five day treatment of niacinamide, and (B/A) a five day treatment of niacinamide followed by a five day treatment of *Tiliacora triandra*. Columns marked with a "*" indicate statistical significance.
Figure 14:
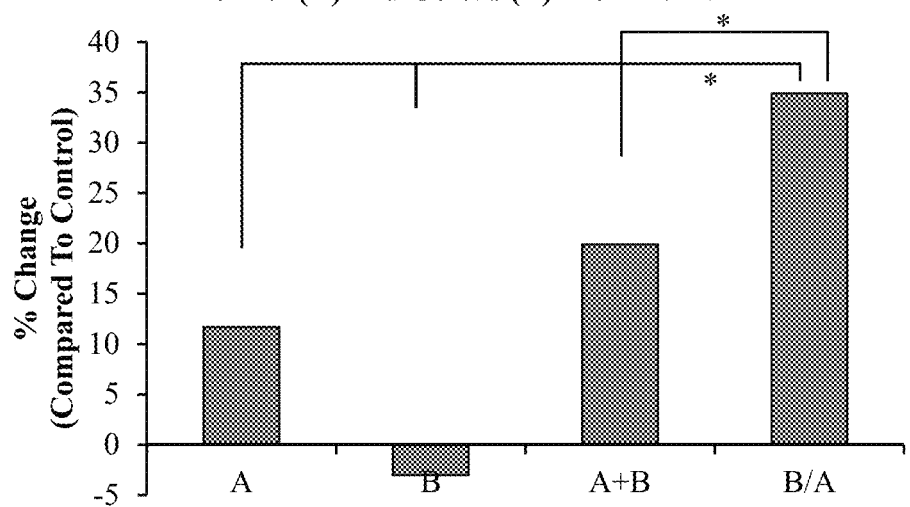
FIG. 14 is a plot of the percentage change from a control in the amount of hyaluronic acid produced in human dermal fibroblast when exposed to (1) a ten day treatment of retinol ("A"), (2) a ten day treatment of *coleus* ("B"), (3) a ten day treatment of retinol and *coleus* ("A+B"), (4) a five day treatment of retinol followed by a five day treatment of *coleus* ("A/B"), and (5) a five day treatment of *coleus* followed by a five day treatment of retinol ("B/A"). Columns marked with a "*" indicate statistical significance.
Figure 15:
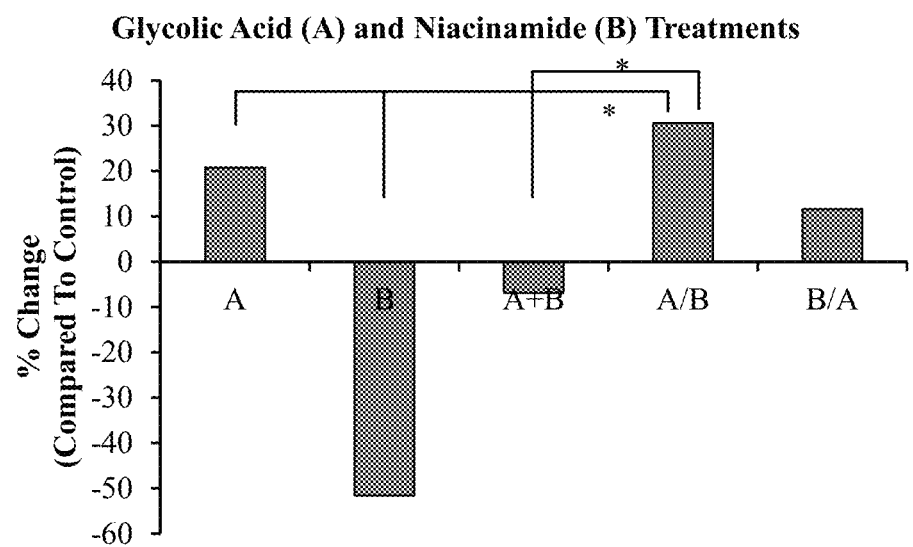
FIG. 15 is a plot of the percentage change from a control in the amount of hyaluronic acid produced in human dermal fibroblast when exposed to (1) a ten day treatment of niacinamide ("A"), (2) a ten day treatment of glycolic acid ("B"), (3) a ten day treatment of niacinamide and glycolic acid ("A+B"), (4) a five day treatment of niacinamide followed by a five day treatment of glycolic acid ("A/B"), and (5) a five day treatment of glycolic acid followed by a five day treatment of niacinamide ("B/A"). Columns marked with a "*" indicate statistical significance.
Figure 16:
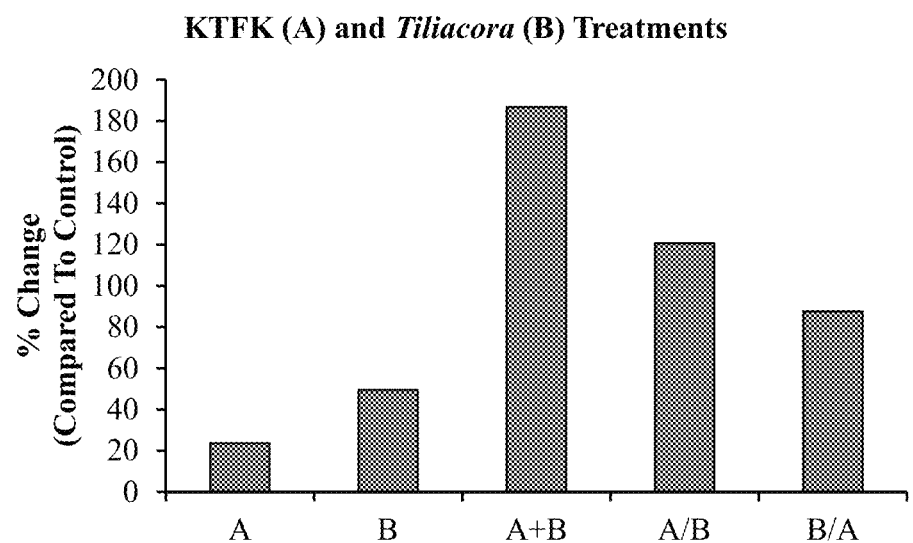
FIG. 16 is a plot of the percentage change from a control in the amount of hyaluronic acid produced in human dermal fibroblast when exposed to (1) a ten day treatment of KTFK ("A"), (2) a ten day treatment of hydroponic *Tiliacora triandra* extract ("B"), (3) a ten day treatment of KTFK and *Tiliacora triandra* ("A+B"), (4) a five day treatment of KTFK followed by a five day treatment of *Tiliacora triandra* ("A/B"), and (5) a five day treatment of *Tiliacora triandra* followed by a five day treatment of KTFK ("B/A").
Figure 17:
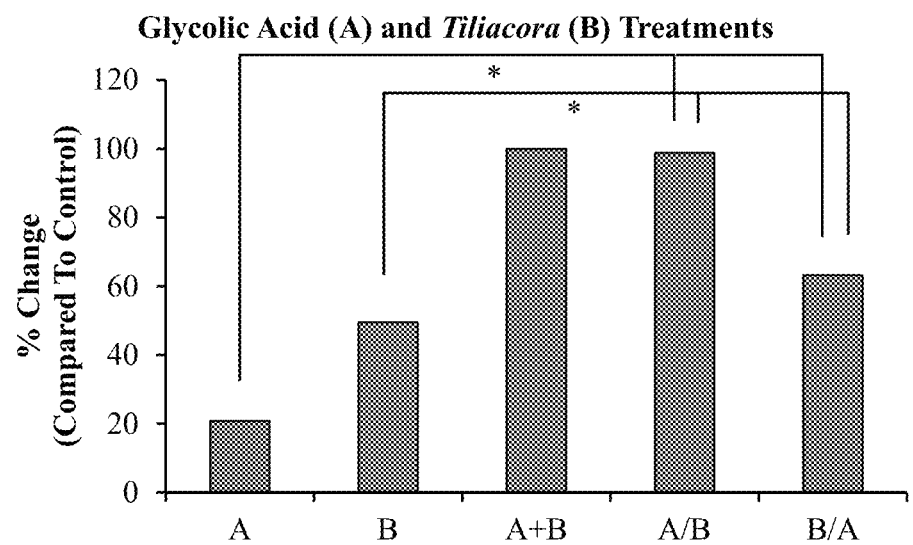
FIG. 17 is a plot of the percentage change from a control in the amount of hyaluronic acid produced in human dermal fibroblast when exposed to (1) a ten day treatment of glycolic acid ("A"), (2) a ten day treatment of hydroponic *Tiliacora triandra* extract ("B"), (3) a ten day treatment of glycolic acid and *Tiliacora triandra* ("A+B"), (4) a five day treatment of *Tiliacora triandra* followed by a five day treatment of glycolic acid ("A/B"), and (5) a five day treatment of glycolic acid followed by a five day treatment of *Tiliacora triandra* ("B/A"). Columns marked with a "*" indicate statistical significance.

Referring now to FIGS. 7 and 8, a skincare product 10 is illustrated comprising a container 12 comprising a first reservoir 14 containing a first skin treatment composition 60 and a second reservoir 16 containing a second skin treatment composition 62, different from said first skin treatment composition, a first pump 26 in fluid communication with the first reservoir 14 for dispensing said first skin treatment composition, and a second pump 22 in fluid communication with the second reservoir 16 for dispensing said second skin treatment composition. The first and second pumps may be the same or different. Any suitable pump used in personal care or cosmetic arts is contemplated to be suitable. FIG. 7 shows a view illustrating the internal contents of reservoirs 14 and 16 distinguished as a first composition 60 and a second composition 62. Referring to FIGS. 9-11, cross sectional views of the product 10 are shown. As illustrated, the pumping mechanisms 20 and 22, in this embodiment, comprise tubes 21 and 23 for conveying liquid compositions from each reservoir and dispensing them through orifices 26 and 28. Springs 25 and 27 actuate the pump according to well-known designs. A barrier 40 separates the first reservoir from the second reservoir. Barrier 40 may be integral with the container 12 such that the two reservoirs cannot be separated from one another. Removable caps 30 and 32 are attached at each respective end of the container and cover the pumps 20 and 22 when seated on the container. Referring to FIGS. 12A and 12B, an embodiment of the skincare product is shown, wherein the exterior of the container or its labeling affixed thereto bears alpha-numeric indicators "1" and "2" distinguishing the first and second reservoirs. The product according to this embodiment, may include visible identifiers 50 indicating each day of the week, for example, printed on a label affixed to the container. In FIG. 12B, the product has a circular sticker 55 placed by the user onto the appropriate day of the week on which the treatment regimen began (for example, Monday or "M"), to serve as a reminder to alternate between the first and second treatment compositions every week on that particular day.

In another embodiment, a plurality of compositions may be contained in a plurality of separate reservoirs within a single container, wherein the container contains a pump in fluid communication with the reservoir containing the first composition for dispensing said first composition and a pump in fluid communication with the reservoir containing the second composition for dispensing said second composition, wherein the pumps form a multi-sided toggle mechanism (e.g., toggle pump), such that actuation of the toggle mechanism to deliver a first composition will prime the actuating mechanism to deliver a second composition optionally while preventing actuation of the toggle mechanism to deliver the first or any other composition until the primed toggle is actuated to deliver the second composition.

In another embodiment, a plurality of single-use, optionally refillable capsules may be utilized, each capsule comprising a reservoir containing a unit dose of a topical composition and a dispenser for dispensing said composition, wherein at least one of said capsules contains a first topical composition and at least one of said capsules contains a second topical composition; wherein the plurality of capsules are removably attached directly or indirectly to one another, and may be individually separated from the plurality prior to dispensing the topical composition contain therein.

In another embodiment, the capsules containing said first topical composition are visually distinct from the capsules containing said second topical composition.

In another embodiment, the dispenser comprises a breakable plug configured to expose an orifice in said capsule when broken.

In another embodiment, the first and second compositions are contained in separate reservoirs within a single container, wherein at least one of the compositions is in the form of a clear gel, and at least a portion of the wall of said container is transparent or translucent such that the first and/or second composition is visible through said portion of said container wall, and wherein the container has an indicator for illuminating said clear gel composition to indicate when that composition should be applied.

In another embodiment, a plurality of compositions are contained in separate reservoirs within a single container, and wherein a rotating dispenser is configured to dispense either the first composition or the second composition through a common opening depending on the degree of rotation of the rotating dispenser.

In another embodiment, a kit or method is utilized comprising: (i) one or more compositions comprising a physiologically acceptable vehicle and an effective amount of a skincare active; (ii) at least one device for imparting mechanical or electromagnetic energy to the skin, and (iii) written instructions for topically applying said first topical compositions for a first period of time and using said device on the same area of skin for a second period of time, in any order, and repeating one or more times. The device may impart light; irradiate; deliver a radio frequency; deliver heat; deliver an electrical current; deliver cold; buff; exfoliate; impart suction; oxygenate; or otherwise apply a phenomenon to the skin.

EXAMPLES

The following example illustrates a specific aspect of the instant description. The example should not be construed as limiting, as the example merely provides specific understanding and practice of the embodiments and its various aspects. In each of the following examples that use an extract of the *Tiliacora triandra* plant, the extract was prepared from hydroponically grown *Tiliacora triandra* and extracted with a 80/20 (v/v) ethanol/water solvent.

Example 1

Human dermal fibroblast cells were grown in a 6-well plate in DMEM media (available from Corning, N.Y.) supplemented with 10% Fetal Bovine Serum (FBS) and L-glutamine ($1.5\times10^5$ cells/plate) overnight. After reaching about 75% confluence, cells were transferred into DMEM media without FBS and incubated for 4-6 hours. Next, the cells were treated with either 0.0001% phytol or 1 µM retinol. Treatment with either phytol alone, or retinol alone was performed in DMEM media without FBS for 16 days. For sequential treatments, the cells were treated with 0.0001% phytol for 6 days followed by 1 µM retinol for 10 days, or with 1 µM retinol for 6 days, followed by 0.0001% phytol for 10 days. Every other day, media were collected and cells were re-treated with phytol or retinol in the same fashion. After treatment, the amount of collagen secreted into the culture media was determined using the HTRF human pro-collagen I kit (available from CISBIO, Inc).

Figure 2:
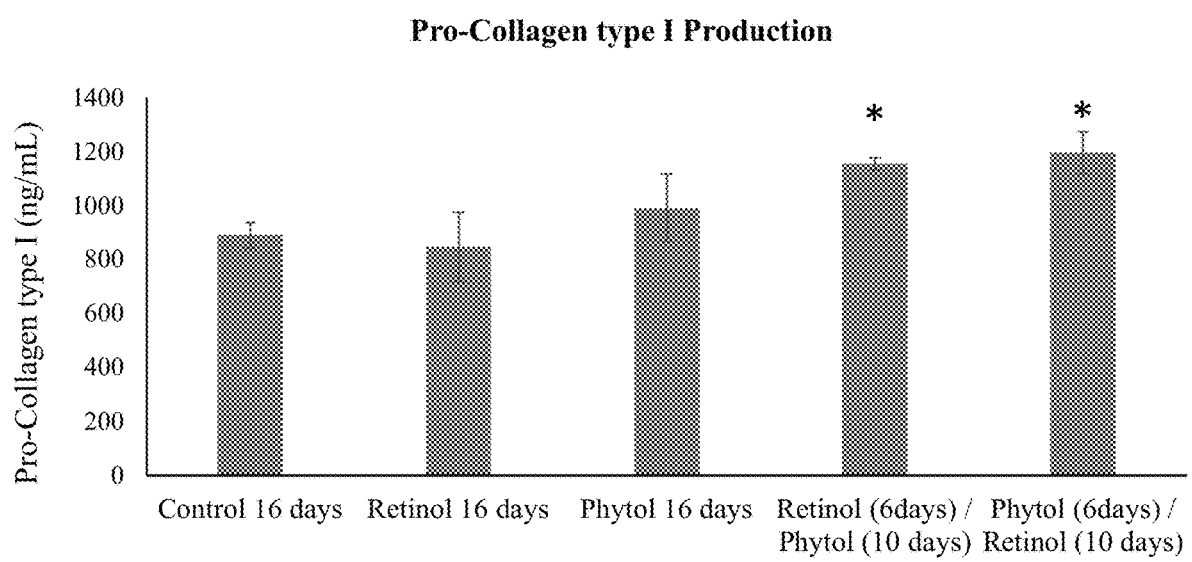
FIG. 2 is a plot of pro-collagen I production in cells treated with (i) phytol alone for 16 days, (ii) retinol alone for 16 days, (iii) retinol alone for 6 days followed by phytol alone for 10 days, (iv) phytol alone for 6 days followed by retinol alone for 10 days, as well as (v) untreated control cells.
Figure 4:
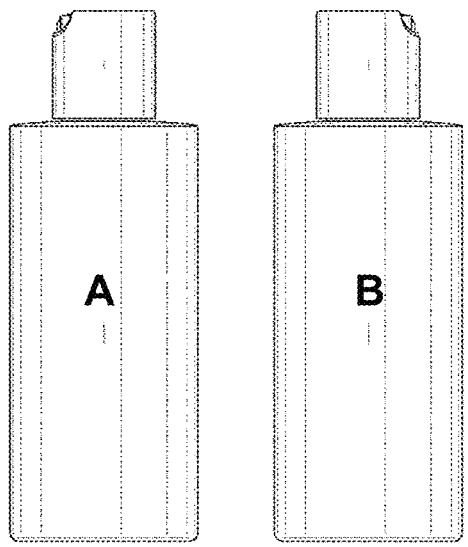
FIG. 4 and FIG. 5 are examples of packaging embodiments of the present invention.
Figure 5:
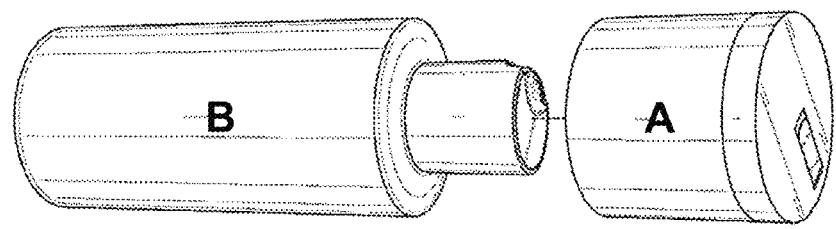

The results are shown in FIGS. 1-2. FIG. 1 depicts levels of pro-collagen in the cells treated with either phytol or retinol alone. The pro-collagen production declines for both phytol- and retinol-treated cells after day 13 despite continuing treatment. FIG. 2 shows collagen production for untreated ("control") cells, phytol-treated cells, retinol-treated cells, as well as cells first treated with retinol followed by phytol, and cells first treated with phytol followed by retinol. It is apparent that cells treated in sequential fashion show increased collagen production as compared to cells treated with a single active.

Example 2

The clinical efficacy of a rotational regimen was demonstrated as follows.

Subjects (age range: 24-59) having mild-to-moderate fine lines and wrinkles were recruited for the study. The subjects were allocated to two groups: Cell 1 received a treatment regimen comprising topical application of an α-hydroxy acid (AHA) formulation once daily for one week followed by topical application of a retinol formulation once daily to the same area of skin on the face for one week. These treatments were continued in rotating fashion for a total of 12 weeks. The subjects in Cell 2 received only the topical retinol treatment once daily for the entire 12 weeks. All subjects underwent a two week pre-conditioning during which they received no AHA or retinol therapy. All subjects applied a sunscreen to the face daily during the conditioning period and throughout the 12 week trial.

The α-hydroxy acid (AHA), e.g., glycolic acid, and Retinol formulations that were used in this study are provided below in Table 1.

TABLE 1

| Ingredient | AHA Formula (wt. %) | Retinol Formula (wt. %) |
|---|---|---|
| Oil-in-water emulsion base | q.s. | q.s. |
| Retinol | — | 0.1 |
| Glycolic Acid (70%) | 4.63 | — |
| Phytol | 1 | — |
| Sodium Ascorbate | — | 0.2 |
| Thiodipropionic Acid | 1 | — |
| Trioxaundecanedioic Acid (90%) | 1.4 | — |

The area of application was evaluated and scored by a dermatologist at baseline and after 4, 8, and 12 weeks.

The results are summarized below in Table 2.

TABLE 2

Mean % Magnitude of Improvement from Baseline
90th Percentile Magnitude of Improvement from Baseline
[% of Panelists with Improvement from Baseline]

| | Week 4 | | Week 8 | | Week 12 | |
|---|---|---|---|---|---|---|
| Parameter | Cell 1 (N = 32) | Cell 2 (N = 32) | Cell 1 (N = 31) | Cell 2 (N = 31) | Cell 1 (N = 31) | Cell 2 (N = 31) |
| Texture | 36 | 35 | 39 | 40 | 44 | 43 |
| | 50 | 50 | 50 | 50 | 60 | 50 |
| | [97] | [100] | [97] | [100] | [97] | [100] |
| Even Skin Tone | 23 | 20 | 29 | 25 | 33 | 30 |
| | 33 | 33 | 40 | 40 | 50 | 50 |
| | [81] | [74] | [97] | [84] | [97] | [90] |

TABLE 2-continued

Mean % Magnitude of Improvement from Baseline
90th Percentile Magnitude of Improvement from Baseline
[% of Panelists with Improvement from Baseline]

| Parameter | Week 4 | | Week 8 | | Week 12 | |
|---|---|---|---|---|---|---|
| | Cell 1 (N = 32) | Cell 2 (N = 32) | Cell 1 (N = 31) | Cell 2 (N = 31) | Cell 1 (N = 31) | Cell 2 (N = 31) |
| Lack of Clarity | 34 | 29 | 38 | 35 | 42 | 37 |
| | 50 | 50 | 50 | 50 | 60 | 50 |
| | [100] | [94] | [100] | [100] | [100] | [97] |
| Discrete Pigmentation | 14 | 9 | 19 | 17 | 25 | 19 |
| | 33 | 50 | 50 | 50 | 50 | 50 |
| | [42] | [19] | [52] | [45] | [58] | [55] |
| Mottled Pigmentation | 18 | — | 23 | 15 | 29 | 19 |
| | 50 | | 50 | 50 | 67 | 50 |
| | [48] | | [52] | [42] | [61] | [52] |
| Fine Wrinkles (Overall) | 24 | 22 | 34 | 32 | 45* | 40 |
| | 25 | 25 | 50 | 50 | 50 | 50 |
| | [94] | [84] | [100] | [100] | [100] | [100] |
| Coarse Wrinkles (Overall) | 6 | 7 | 20 | 19 | 22 | 20 |
| | 25 | 25 | 33 | 33 | 40 | 33 |
| | [23] | [26] | [77] | [71] | [77] | [74] |

*Statistically significant ($p \leq 0.05$) improvement over retinol treatment (Cell 2).

As shown in Table 2, improvements from baseline were noted as early as four weeks after the start of the study, with marked improvements in skin tone, clarity, and reduction in discrete pigmentation. By twelve weeks a statistically significant reduction in the appearance of fine lines was found for the rotational treatment group (Cell 2) compared to the retinol treatment group (Cell 1). This result was surprising because the rotational group (Cell 1) received half the total dose of retinol that the retinol group received, and AHA therapy is not generally regarding as being capable of achieving the magnitude of wrinkle/fine line reduction as retinol.

Examples 3-10

Hyaluronic Acid (HA) Assessment in Human Dermal Fibroblasts

A series of experiments was conducted to assess the effects of the treatment regimens of active ingredients on the production of hyaluronic acid (HA) in human dermal fibroblast (HDF) cells. The following five treatment regimens were assessed: (1) active ingredient A, alone; (2) active ingredient B, alone; (3) the combination of active ingredients A+B; (4) active ingredient A, alone, followed by active ingredient B, alone ("A/B"); and (5) active ingredient B, alone, followed by active ingredient A, alone ("B/A"). For treatment regimens (1), (2), and (3), the active ingredients were administered to cells for 10 consecutive days. For treatment regimens (4) and (5) (sequential regimens), the cells were treated with active ingredient A or active ingredient B for 5 days, followed by active ingredient B or active ingredient A for 5 days, respectively.

Human dermal fibroblast cells were grown in 96-well plates in DMEM media (available from CORNING, N.Y.) supplemented with 10% FBS and L-glutamine. After reaching about 75% confluence, cells were transferred into DMEM media without FBS, and incubated for 4-6 hours. Different wells were assigned to one of treatment regimens (1)-(5) as described above, with six wells allocated to each treatment regimen (i.e., n=6). All active ingredients were prepared as emulsions and applied directly to the HDF cells. The specific active ingredients used in each of the five treatment regimens are provided below in Table 3. Following treatment, cells were collected and the amount of hyaluronic acid (HA) secreted from the cells was measured using a commercially available HA assay (available from CORGENIX Inc., CO).

TABLE 3

| Ex. | Active A | [A] | Active B | [B] |
|---|---|---|---|---|
| 3 | Tiliacora triandra | 0.10% | Niacinamide | 0.10% |
| 4 | Retinol | 1 µM | Coleus forskohlii | 0.001% |
| 5 | Glycolic Acid | 1 mM | Niacinamide | 0.1% |
| 6 | KTFK | 0.001% | Tiliacora triandra | 0.1% |
| 7 | Glycolic Acid | 1 mM | Tiliacora triandra | 0.1% |
| 8 | Glycolic Acid | 1 mM | Tetrapeptide 4 | 0.10% |
| 9 | Sodium Glycolate | 10 µM | Phytol | 0.010% |
| 10 | Sodium Glycolate | 10 µM | Retinol | 1 µM |

The results are summarized below in Table 4 and plotted in FIGS. 13-17 as a percentage change over control (i.e. cells treated with the same emulsion but in absence of active ingredients).

TABLE 4

| Ex. | A alone (% change in HA) | B alone (% change in HA) | A + B (% change in HA) | A/B (% change in HA) | B/A (% change in HA) |
|---|---|---|---|---|---|
| 3 | 49.5 | −51.6 | 7.87 | 45.2 | 80.2 |
| 4 | 11.7 | −3.04 | 19.9 | — | 34.9 |
| 5 | 20.8 | −51.6 | −6.9 | 30.6 | 11.6 |
| 6 | 23.7 | 49.5 | 186.7 | 120.7 | 87.6 |
| 7 | 20.8 | 49.5 | 100 | 98.8 | 63.2 |
| 8 | 20.8 | 15.1 | 38.1 | −5.52 | 0.0 |
| 9 | −2.54 | 67.7 | −6.47 | 15.6 | — |
| 10 | −2.54 | 11.7 | 27.5 | 26.3 | — |

As shown in Table 4 and FIGS. 13-17, sequential treatment of certain active ingredients is effective in stimulating HA production. The sequential treatment resulted in a more than additive improvement in Examples 3-6 and 10. Examples 3-5 and 10 each showed statistically significantly greater production of HA, compared with when those active ingredients are used alone or simultaneously. For example, Example 3 (see FIG. 11) demonstrates that sequential treatment of niacinamide followed by *Tiliacora triandra* extract results in higher levels of HA produced than with treatment by *Tiliacora triandra* alone, niacinamide alone, or simultaneous application of *Tiliacora triandra* and niacinamide.

Example 11

Measurement of HA in Full Thickness 3D Skin Models for Rotational Treatment Regimens.

A series of experiments was conducted to assess the effects of the treatment regimens of glycolic acid and *Tiliacora triandra* on the production of hyaluronic acid (HA) on full thickness 3D skin cultures. Five different treatment regimens were assessed: (1) 4% glycolic acid, alone; (2) 0.2% *Tiliacora triandra*, alone; (3) the combination of 4% glycolic acid+0.2% *Tiliacora triandra*; (4) 4% glycolic acid, alone, followed by 0.2% *Tiliacora triandra*, alone; and (5) 0.2% *Tiliacora triandra*, alone, followed by 4% glycolic acid, alone. Glycolic acid was administered topically to the 3D tissue and *Tiliacora triandra* was administered via the growth media. For treatment regimens (1), (2), and (3), the active ingredient or ingredients were applied to cells for 4 consecutive days. For treatment regimens (4) and (5) (sequential regimens), the cells were treated with glycolic acid or *Tiliacora triandra* for 2 days, followed by *Tiliacora triandra* or glycolic acid for 2 days, respectively.

Human 3D skin EFT400FT tissues (MatTek, MA) were cultured following the manufacturer's instructions. Each treatment regimen was applied to twelve 3D skin samples. Different 3D skin samples were assigned to one of treatment regimens (1)-(5) as described above, with twelve skin tissue models allocated to each treatment regimen (i.e., n=12). Following treatment, cells were collected and the amount of hyaluronic acid secreted from the cells was measured using a commercially available HA assay (available from COR-GENIX Inc., CO).

TABLE 5

| Glycolic Acid | *Tiliacora triandra* | Glycolic Acid + *Tiliacora triandra* | Glycolic Acid/ *Tiliacora triandra* | *Tiliacora triandra*/ Glycolic Acid |
|---|---|---|---|---|
| 42.6 | 36.1 | 79.2 | 88.4 | −29.4 |

Figure 18:
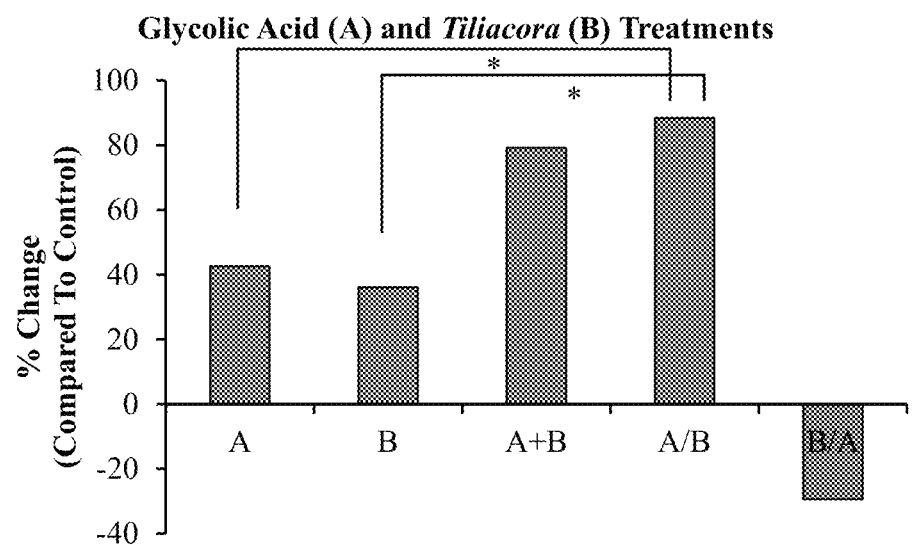
FIG. 18 is a plot of the percentage change from a control in the amount of hyaluronic acid produced in full thickness 3D models when exposed to (1) a ten day treatment of glycolic acid ("A"), (2) a ten day treatment of hydropnic *Tiliacora triandra* extract ("B"), (3) a ten day treatment of glycolic acid and *Tiliacora triandra* ("A+B"), (4) a five day treatment of glycolic acid followed by a five day treatment of *Tiliacora triandra* ("A/B"), and (5) a five day treatment of glycolic acid followed by a five day treatment of *Tiliacora triandra* ("B/A"). Columns marked with a "*" indicate statistical significance.

The results are shown in Table 5 and plotted in FIG. 18 as a percentage change over control (i.e., models treated with the same emulsion but in absence of active ingredients). Sequential treatment with glycolic acid followed by *Tiliacora triandra* extract is effective in stimulating HA production. Example 11 (see FIG. 16) demonstrates that a sequential treatment of glycolic acid followed by *Tiliacora triandra* results in statistically significant higher levels of HA produced than with treatment by either active alone.

Examples 12-13

Pro-Collagen Type I Assessment in Human Dermal Fibroblasts

A series of experiments was conducted to assess the effects of the treatment regimens of active ingredients shown in Table 6 on the production of pro-collagen type I in human dermal fibroblast (HDF) cells. Five different treatment regimens were assessed: (1) active ingredient A, alone; (2) active ingredient B, alone; (3) the combination of active ingredients A+B; (4) active ingredient A, alone, followed by active ingredient B, alone; and (5) active ingredient B, alone, followed by active ingredient A, alone. For treatment regimens (1), (2), and (3), the active ingredients were applied to cells for 10 consecutive days. For treatment regimens (4) and (5) (sequential regimens), the cells were treated with either active ingredient A or B for 5 days, followed by treatment with the other active ingredient B or A for 5 days, respectively.

Human dermal fibroblast cells were grown in 96-well plates in DMEM media (available from CORNING, N.Y.) supplemented with 10% FBS and L-glutamine. After reaching about 75% confluence, cells were transferred into DMEM media without FBS, and incubated for 4-6 hours. Different wells were assigned to one of treatment regimens (1)-(5) as described above, with six wells allocated to each treatment regimen. All active ingredients were prepared as emulsions and applied directly to the HDF cells. The specific active ingredients used in each of the five treatment regimens are provided below in Table 6. Following treatment, measurements on the amount of pro-collagen produced from the cells were performed using a commercially available pro-collagen type I enzyme-linked immuno sorbent assay (ELISA) kit (available from TAKARA Inc., KR).

TABLE 6

| Ex. | Active A | [A] | Active B | [B] |
|---|---|---|---|---|
| 12 | Retinol | 1 μM | *Coleus forskohlii* | 0.001% |
| 13 | Phytol | 0.0001% | Retinol | 1 μM |

Figure 19:
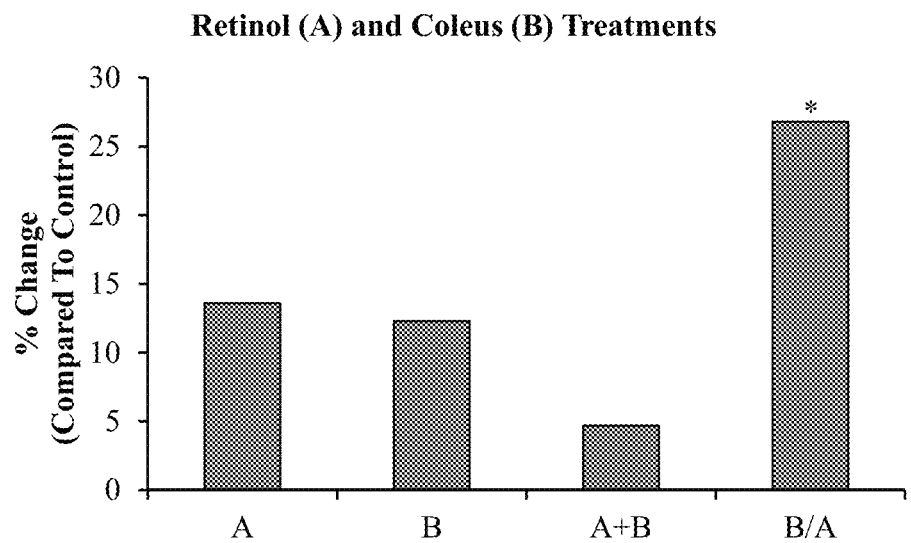
FIG. 19 is a plot of the percentage change from a control in the amount of pro-collagen type I produced in human dermal fibroblasts when exposed to (1) a ten day treatment of retinol and *Coleus forskohlii* ("A+B"), and (4) a five day treatment of *Coleus forskohlii* followed by a five day treatment of retinol ("B/A"). The column marked with a "*" indicate statistical significance.
Figure 20:
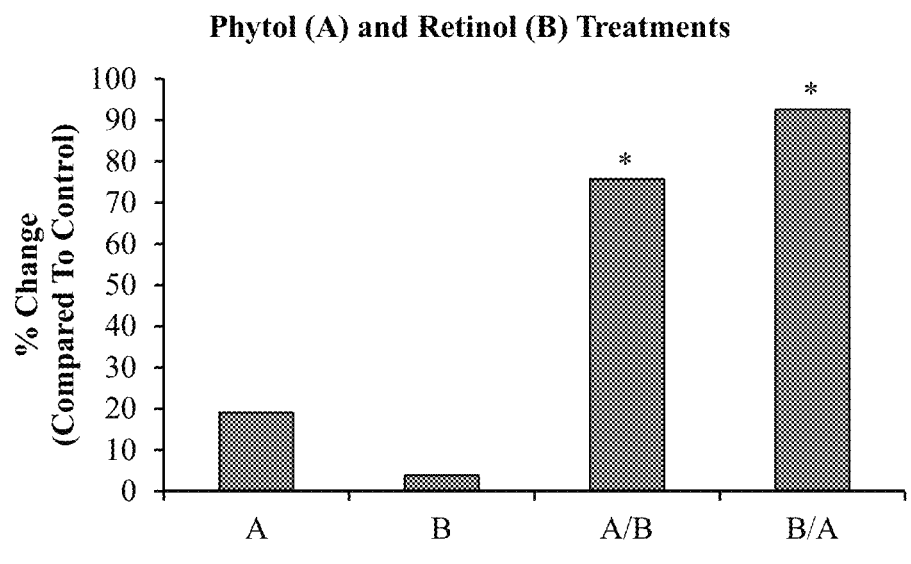
FIG. 20 is a plot of the percentage change from a control in the amount of pro-collagen type I produced in human dermal fibroblasts when exposed to (1) a ten day treatment of phytol ("A"), (2) a ten day treatment of retinol ("B"), (3) a five day treatment of phytol followed by a five day treatment of retinol ("A/B"), and (4) a five day treatment of retinol followed by a five day treatment of phytol ("B/A"). The columns marked with a "*" indicate statistical significance.

The results are shown in Table 7 and plotted in FIGS. 19-20 as a percentage change from control (i.e., cells treated with same emulsion but in absence of active ingredients).

TABLE 7

| Ex. | A alone (% change in pro-collagen) | B alone (% change in pro-collagen) | A + B (% change in pro-collagen) | A/B (% change in pro-collagen) | B/A (% change in pro-collagen) |
|---|---|---|---|---|---|
| 12 | 13.6 | 12.3 | 4.7 | — | 26.8 |
| 13 | 19.1 | 3.9 | — | 75.7 | 92.6 |

As shown in Table 7, sequential treatment of *Coleus forskohlii* extract followed by retinol in human dermal fibroblast cells results in statistically significant improvement in pro-collagen type I production as compared to treatment using retinol alone, *Coleus forskohlii* alone, or simultaneous application of retinol and *Coleus forskohlii*. Similarly, it is apparent that sequential treatments of phytol/retinol (AB) and retinol/phytol (B/A) on HDF cells produce statistically significantly more pro-collage type I than treatments to cells with either active. The sequential treatment of retinol/phytol resulted in a more than additive improvement in Example 13.

Examples 14-16

Melanin in 3D Skin Models

A series of experiments was conducted to assess the effects of treatment regimens of active ingredients shown in Table 8 on the production of melanin in 3D models. Four different treatment regimens were assessed: (1) active ingredient A, alone; (2) active ingredient B, alone; (3) the combination of active ingredients A+B; and (4) active ingredient A, alone, followed by active ingredient B, alone, as detailed in Table 8. For treatment regimens (1), (2), and (3), the active ingredients were applied to cells for 14 consecutive days. For treatment regimen (4) (sequential regimen), the cells were treated with active ingredient A for 7 days, followed by treatment with the other active ingredient B for 7 days.

TABLE 8

| Ex. | Active A | [A] | Active B | [B] |
|---|---|---|---|---|
| 14 | Niacinamide | 0.1% | Hexylresorcinol | 0.05% |
| 15 | TDPA | 1% | Niacinamide | 0.1% |
| 16 | TDPA | 1% | Hexylresorcinol | 0.05% |

Human 3D MelanoDerm MEL-B skin tissues (available from MatTek, MA) were cultured following the manufacture instructions. Different skin tissue models were assigned to one of treatment regimens (1)-(4) as described above, with six models allocated to each treatment regimen (i.e., n=6). All active ingredients were prepared as emulsions and applied directly to the skin models. The specific active ingredients used in each of the four treatment regimens are provided in Table 8. Following treatment, skin tissue models were collected and the amount of melanin produced from the cells was measured using a SOLVABLE melanin assay. Treated skin tissues were prepared using a phosphate buffer saline and sodium bicarbonate. Each skin tissue is added to 500 μl of 0.5 M SOLVABLE solubilizer (available from Packard BioScience) and incubated at 95° overnight. The absorbance of each skin tissue sample is measured at 490 nm and the absorbance is compared to a standard curve to indicate the amount of melanin produced and pigmentation in each skin tissue model.

TABLE 9

| Ex. | A (% change in pigmentation) | B (% change in pigmentation) | A + B (% change in pigmentation) | A/B (% change in pigmentation) |
|---|---|---|---|---|
| 14 | −18.9 | 140.4 | 95.9 | 77.8 |
| 15 | −19.1 | −18.9 | −24.2 | −20.4 |
| 16 | −19.1 | 140.4 | 34.1 | 39.7 |

The results for treatments measuring the melanin content produced are shown in Table 9 as a percentage change from control (i.e., untreated samples or samples treated with the same emulsion but in absence of active ingredients).

Example 17

Hyaluronic Assessment in Human Dermal Fibroblasts in Response to Pulsed Treatment Regimens A series of experiments was conducted to assess the effects of different treatment regimens of active ingredients shown in Table 9 on the production of hyaluronic acid (HA) in human dermal fibroblast (HDF) cells. Two different treatment regimens were assessed: (1) active ingredient A applied to cells for 12 consecutive days; and (2) active ingredient applied to cells for 2 consecutive days followed by application of media not containing active ingredient for two consecutive days repeatedly until treatment is applied for 12 consecutive days.

Human dermal fibroblast cells were grown in 96-well plates in DMEM media (available from CORNING, N.Y.) supplemented with 10% FBS and L-glutamine. After reaching about 75% confluence, cells were transferred into DMEM media without FBS, and incubated for 4-6 hours. Different wells were assigned to one of treatment regimens (1)-(2) as described above, with six wells allocated to each treatment regimen. All active ingredients were prepared as emulsions and applied directly to the HDF cells. The specific active ingredients used in each of the two treatment regimens are provided below in Table 10. Following treatment, cells were collected and the amount of hyaluronic acid (HA) secreted from the cells was measured using a commercially available HA assay (available from CORGENIX Inc., CO).

TABLE 10

| Active Ingredient | Active Conc. | % Change in HA over control (daily) | % Change in HA over control (pulsed) |
|---|---|---|---|
| *Tiliacora triandra* | 0.05% | 184.1 | 127.7 |
| Niacinamide | 0.10% | −36.5 | 1.3 |
| Glycolic Acid | 1 mM | 9.1 | 5.1 |
| Retinol | 1 μM | 17.2 | 32.0 |
| Phytol | 0.01% | −4.0 | 25.1 |

The results are summarized in Table 10 as a percentage change over control (i.e., cells treated with same emulsion but in absence of active ingredients). As shown in Table 10, pulsed treatment of phytol, and retinol resulted in significantly more production of hyaluronic acid than in daily treatment regimens of actives to HDF cells. Further, pulsed treatment with *Tiliacora triandra* or glycolic acid was only slightly less effective than daily treatment, despite the fact that over the entire treatment duration, half as much active was used in the pulsed treatment as compared to daily treatment.

As various changes can be made in the above-described subject matter without departing from the scope and spirit of the present invention, it is intended that all subject matter contained in the above description, or defined in the appended claims, be interpreted as descriptive and illustrative of the present invention. Many modifications and variations of the present invention are possible in light of the above teachings. Accordingly, the present description is intended to embrace all such alternatives, modifications, and variances which fall within the scope of the appended claims.

The invention claimed is:

1. A method for diminishing dermatological signs of aging in human skin comprising, in any order, the steps of (1) topically applying to an area of the skin in need thereof, at least once daily, a first skin treatment composition comprising, in a physiologically compatible vehicle, an effective amount of an extract of *Tiliacora triandra* for a first period of time comprising from 2 to 15 days; (2) topically applying to said skin, at least once daily, a second skin treatment composition that is different from said first skin treatment composition for a second period of time comprising from 2 to 15 days wherein said second skin treatment composition comprises a moisturizer; and (3) repeating steps (1) and (2) for a number of times sufficient to diminish said dermatological signs of skin aging.

2. The method according to claim 1, wherein said second skin treatment composition comprises a peptide.

3. The method according to claim 2, wherein said peptide is selected from the group consisting of K-ava-K; KTFK; and n-acetyl tyrosinamide.

4. The method according to claim 1, wherein said second skin treatment composition comprises niacinamide.

5. The method according to claim 1, wherein said second skin treatment composition comprises an alpha-hydroxy acid or salt thereof.

6. The method according to claim 1, wherein said diminishing dermatological signs of aging is selected from the group consisting of:
(a) treatment, reduction, and/or prevention of fine lines and/or wrinkles;
(b) reduction of skin pore size;
(c) improvement in skin thickness, plumpness, and/or tautness;
(d) improvement in skin smoothness, suppleness and/or softness;
(e) improvement in skin tone, radiance, and/or clarity;
(f) improvement in procollagen, and/or collagen production;
(g) improvement in maintenance and remodeling of elastin;
(h) improvement in skin texture and/or promotion of retexturization;
(i) improvement in skin barrier repair and/or function;
(j) improvement in appearance of skin contours;
(k) restoration of skin luster and/or brightness;
(l) replenishment of essential nutrients and or constituents in the skin;
(m) improvement of skin appearance decreased by aging and/or menopause;
(n) improvement in skin moisturization;
(o) increase in skin elasticity and/or resiliency;
(p) treatment, reduction, and/or prevention of skin sagging;
(q) improvement in skin firmness;
(r) reduction of pigment spots and/or mottled skin; and
(s) improvement of optical properties of skin by light diffraction or reflection.

7. The method according to claim 6, wherein said alpha-hydroxy acid or salt thereof comprises glycolic acid or a salt thereof.

8. The method according to claim 1, wherein said first period of time is 7 days, and said second period of time is 7 days.

9. The method according to claim 1, wherein said first and second periods of time are consecutive such that one begins on the day following the last day of the other.

10. The method according to claim 1, wherein said second skin treatment composition does not comprise an effective amount of *Tiliacora triandra*.

\* \* \* \* \*